(12) United States Patent
Lai et al.

(10) Patent No.: US 9,150,637 B2
(45) Date of Patent: Oct. 6, 2015

(54) VARIANT OF ANTIHEMOPHILIC FACTOR VIII HAVING INCREASED SPECIFIC ACTIVITY

(75) Inventors: Chee Kong Lai, Littleton, MA (US); Roddy Kevin Stafford, Shrewsbury, MA (US)

(73) Assignees: BAXALTA INC., Bannockburn, IL (US); BAXALTA GMBH, Glattpark (Opfikon) (CH)

( * ) Notice: Subject to any disclaimer, the term of this patent is extended or adjusted under 35 U.S.C. 154(b) by 0 days.

(21) Appl. No.: 13/883,244

(22) PCT Filed: Nov. 4, 2011

(86) PCT No.: PCT/US2011/059297
§ 371 (c)(1),
(2), (4) Date: Jul. 23, 2013

(87) PCT Pub. No.: WO2012/061689
PCT Pub. Date: May 10, 2012

(65) Prior Publication Data
US 2013/0296244 A1    Nov. 7, 2013

Related U.S. Application Data

(60) Provisional application No. 61/410,437, filed on Nov. 5, 2010.

(51) Int. Cl.
*A61K 38/38* (2006.01)
*C07K 14/755* (2006.01)
*A61K 38/00* (2006.01)

(52) U.S. Cl.
CPC .............. *C07K 14/755* (2013.01); *A61K 38/00* (2013.01)

(58) Field of Classification Search
None
See application file for complete search history.

(56) References Cited

U.S. PATENT DOCUMENTS

| | | |
|---|---|---|
| 4,348,384 A | 9/1982 | Horikoshi et al. |
| 4,757,006 A | 7/1988 | Toole, Jr. et al. |
| 4,868,112 A | 9/1989 | Toole, Jr. |
| 5,364,771 A | 11/1994 | Lollar et al. |
| 5,384,132 A | 1/1995 | De Meere et al. |
| 5,563,045 A | 10/1996 | Pittman et al. |
| 5,565,427 A | 10/1996 | Freudenberg |
| 5,583,209 A | 12/1996 | Lollar et al. |
| 5,605,884 A | 2/1997 | Lee et al. |
| 5,663,060 A | 9/1997 | Lollar et al. |
| 5,733,873 A | 3/1998 | Osterberg et al. |
| 5,744,446 A | 4/1998 | Lollar et al. |
| 5,763,401 A | 6/1998 | Nayar |
| 5,859,204 A | 1/1999 | Lollar |
| 5,874,408 A | 2/1999 | Nayar |
| 5,888,974 A | 3/1999 | Lollar et al. |
| 5,925,739 A | 7/1999 | Spira et al. |
| 5,935,935 A | 8/1999 | Connelly et al. |
| 5,962,650 A | 10/1999 | Osterberg et al. |
| 5,972,885 A | 10/1999 | Spira et al. |
| 6,024,938 A | 2/2000 | Corbo et al. |
| 6,180,371 B1 | 1/2001 | Lollar |
| 6,200,560 B1 | 3/2001 | Couto et al. |
| 6,376,463 B1 | 4/2002 | Lollar |
| 6,458,563 B1 | 10/2002 | Lollar |
| 6,586,574 B1 | 7/2003 | Hansen |
| 6,642,028 B1 | 11/2003 | Ill et al. |
| 6,759,216 B1 | 7/2004 | Lollar |
| 6,770,744 B2 | 8/2004 | Lollar |
| 6,818,439 B1 | 11/2004 | Jolly et al. |
| 7,012,132 B2 | 3/2006 | Lollar |
| 7,033,791 B2 | 4/2006 | Lollar |
| 7,122,634 B2 | 10/2006 | Lollar |
| 7,560,107 B2 | 7/2009 | Lollar |
| 7,576,181 B2 | 8/2009 | Lollar et al. |
| 7,576,182 B1 | 8/2009 | Goddard et al. |
| 7,790,680 B2 | 9/2010 | White et al. |
| 8,101,718 B2 | 1/2012 | Lollar et al. |
| 8,501,694 B2 | 8/2013 | Lollar et al. |
| 2004/0116345 A1 | 6/2004 | Besman et al. |
| 2004/0147436 A1 | 7/2004 | Kim et al. |
| 2004/0249134 A1 | 12/2004 | Lollar |
| 2005/0009148 A1 | 1/2005 | Lollar |
| 2005/0118684 A1 | 6/2005 | Lollar |
| 2005/0123997 A1 | 6/2005 | Lollar |
| 2007/0135342 A1 | 6/2007 | Lollar |
| 2007/0173446 A1 | 7/2007 | Lollar et al. |
| 2009/0270329 A1* | 10/2009 | Lollar et al. .................... 514/12 |
| 2009/0271163 A1 | 10/2009 | Ngo et al. |
| 2009/0325881 A1 | 12/2009 | Lollar |
| 2010/0075891 A1 | 3/2010 | Ayalon-Soffer et al. |

(Continued)

FOREIGN PATENT DOCUMENTS

| | | |
|---|---|---|
| EP | 0182448 A2 | 5/1986 |
| EP | 0306968 A2 | 3/1989 |

(Continued)

OTHER PUBLICATIONS

Donath et al (Eur J Biochem (1996) 240: 365-372).*
GenBank (NP_999332 "coagulation factor VIII precursor [Sus scrofa]" dated Jan. 26, 2014).*
Genbank Accession No. AAR67709, B-domain deleted factor-VIII, dated Jul. 20, 1995.
Supplemental European Search Report issued in counterpart European Patent Application No. 11838863.6, dated May 22, 2014.
Altschul et al., Basic Local Alignment Search Tool, *J. Mol. Biol.* 215: 403-10 (1990).
Altschul et al., Gapped BLAST and PSI-BLAST: A new generation of protein database search programs, *Nucl. Acids Res.*, 25(17): 3389-402 (1997).
Brandt, Measurement of factor VIII: A potential risk factor for vascular disease, *Arch. Pathol. Lab Med.* 117(1): 48-51 (1993).

(Continued)

*Primary Examiner* — Karlheinz R Skowronek
*Assistant Examiner* — Mindy Newman
(74) *Attorney, Agent, or Firm* — Marshall, Gerstein & Borun LLP

(57) ABSTRACT

The present invention is in the field of hemophilia therapy. It relates to a new variant of antihemophilic factor VIII having increased specific activity in comparison to known factor VIII products.

12 Claims, 7 Drawing Sheets

(56) References Cited

U.S. PATENT DOCUMENTS

| | | |
|---|---|---|
| 2010/0081615 A1 | 4/2010 | Pan et al. |
| 2010/0120664 A1 | 5/2010 | Schulte et al. |

FOREIGN PATENT DOCUMENTS

| | | |
|---|---|---|
| JP | 62-81327 A | 4/1987 |
| JP | 64-85927 | 3/1989 |
| JP | 4-217630 A | 8/1992 |
| JP | 08-99999 | 4/1996 |
| WO | WO-89/09784 A1 | 10/1989 |
| WO | WO-91/07438 A1 | 5/1991 |
| WO | WO-93/20093 A1 | 10/1993 |
| WO | WO-94/07510 A1 | 4/1994 |
| WO | WO-94/11503 A2 | 5/1994 |
| WO | WO-94/29471 A1 | 12/1994 |
| WO | WO-95/24427 A1 | 9/1995 |
| WO | WO-97/03191 A1 | 1/1997 |
| WO | WO-97/03193 A1 | 1/1997 |
| WO | WO-99/46274 A1 | 9/1999 |
| WO | WO-00/48635 A1 | 8/2000 |
| WO | WO-00/71141 A1 | 11/2000 |
| WO | WO-01/03726 A1 | 1/2001 |
| WO | WO-01/68109 A1 | 9/2001 |
| WO | WO-03/080108 A1 | 10/2003 |
| WO | WO-2005/107776 A1 | 11/2005 |

OTHER PUBLICATIONS

Donath et al., Kinetics of factor VIII light-chain cleavage by thrombin and factor Xa. A regulatory role of the factor VIII heavy-chain region Lys713-Arg740. *Eur. J. Biochem.* 240: 365-72 (1996).

GenBank Accession No. NP_999332, Coagulation factor VIII precursor [Sus scrofa], dated Mar. 12, 2010.

Karlin et al., Applications and statistics for multiple high-scoring segments in molecular sequences, *Proc. Natl. Acad. Sci. USA*, 90(12): 5873-7 (1993).

Karlin et al., Methods for assessing the statistical significance of molecular sequence features by using general scoring schemes, *Proc. Natl. Acad. Sci. USA*, 87(6): 2264-8 (1990).

Langdell et al., Effect of antihemophilic factor on one-stage clotting tests: A presumptive test for hemophilia and a simple one-stage antihemophilic assay procedure, *J. Lab Clin. Med.* 41: 637-47 (1953).

Mertens et al., Biological activity of recombinant factor VIII variants lacking the central B-domain and the heavy-chain sequence Lys713-Arg740: discordant in vitro and in vivo activity, *Br. J.Haematol.* 85(1): 133-42 (1993).

Myers et al., Optimal alignments in linear space, *Comput. Appl. Biosci.* 4(1): 11-7 (1988).

National Committee for Clinical Laboratory Standards (NCCLS USA). Determination of factor coagulant activities; Approved guideline, NCCLS Document H-48-A; 17:1-36 (1997).

Newell et al., Acidic residues C-terminal to the A2 domain facilitate thrombin-catalyzed activation of factor VIII. *Biochemistry*, 47(33): 8786-95 (2008).

Ngo et al., Crystal structure of human factor VIII: Implications for the formulation of the factor IXa-factor VIIIa complex. *Structure*, 16(4): 597-606 (2008).

Nogami et al., Exosite-interactive regions in the A1 and A2 domains of factor VIII facilitate thrombin-catalyzed cleavage of heavy chain. *J. Biol. Chem.*, 280(18): 18476-87 (2005).

Osterberg et al., Development of freeze-dried albumin-free formulation of recombinant factor VIII SQ. *Pharmaceut. Res.*, 14(7): 892-8 (1977).

Parker et al., Comparative immunogenicity of recombinant B domain-deleted porcine factor VIII and Hyate:C in hemophilia A mice presensitized to human factor VIII. *J. Thromb. Haemost.*, 2: 605-11 (2004).

Pearson et al., Improved tools for biological sequence comparison, *Proc. Natl. Acad. Sci. USA*, 85(8): 2444-8 (1988).

Pipe, Functional roles of the factor VIII B domain. *Haemophilia*, 15(6): 1187-96 (2009).

Preston et al., Quality control and factor VIII assays, *Haemophilia*, 4: 651-3 (1998).

Sabatino et.al., Recombinant canine B-domain-deleted FVIII exhibits high specific activity and is safe in the canine hemophilia A model, *Blood*, 114(20): 4562-5 (2009).

Thim et al., Purification and characterization of a new recombinant factor VIII (N8). *Haemophilia*, 16(2): 349-59 (2009).

Toole et al., Molecular cloning of a cDNA encoding human antihaemophilic factor, *Nature*, 312(5992): 342-7 (1984).

Van Den Brink et al., Molecular analysis of human anti-factor VIII antibodies by V gene phage display identifies a new epitope in the acidic region following the A2 domain. *Blood*, 96(2): 540-5 (2000).

Vehar et al., Structure of human factor VIII, *Nature*, 312(5992): 337-42 (1984).

Wood et al., Expression of active human factor VIII from recombinant DNA clones, *Nature*, 312(5992): 330-7 (1984).

International Search Report and Written Opinion of the International Searching Authority, United States Patent and Trademark Office, issued in connection with International Application No. PCT/US2011/029297, dated Jul. 5, 2012.

\* cited by examiner

```
                    1                                                   50
HUMFVIII   ATRRYYLGAV ELSWDYMQSD .LGELPVDAR FPPRVPKSFP FNTSVVYKKT
PIGFVIII   AIRRYYLGAV ELSWDYRQSE LLRELHVDTR FPATAPGALP LGPSVLYKKT
MURFVIII   AIRRYYLGAV ELSWNYIQSD LLSVLHTDSR FLPRMSTSFP FNTSIMYKKT
CANFVIII   ATRKYYLGAV ELSWDYMQSD LLSALHADTS FSSRVPGSLP LTTSVTYRKT 51                                                  100
HUMFVIII   LFVEFTDHLF NIAKPRPPWM GLLGPTIQAE VYDTVVITLK NMASHPVSLH
PIGFVIII   VFVEFTDQLF SVARPRPPWM GLLGPTIQAE VYDTVVVTLK NMASHPVSLH
MURFVIII   VFVEYKDQLF NIAKPRPPWM GLLGPTIWTE VHDTVVITLK NMASHPVSLH
CANFVIII   VFVEFTDDLF NIAKPRPPWM GLLGPTIQAE VYDTVVIVLK NMASHPVSLH 101                                                 150
HUMFVIII   AVGVSYWKAS EGAEYDDQTS QREKEDDKVF PGGSHTYVWQ VLKENGPMAS
PIGFVIII   AVGVSFWKSS EGAEYEDHTS QREKEDDKVL PGKSQTYVWQ VLKENGPIAS
MURFVIII   AVGVSYWKAS EGDEYEDQTS QMEKEDDKVF PGESHTYVWQ VLKENGPMAS
CANFVIII   AVGVSYWKAS EGAEYEDQTS QKEKEDDNVI PGESHTYVWQ VLKENGPMAS 151                                                 200
HUMFVIII   DPLCLTYSYL SHVDLVKDLN SGLIGALLVC REGSLAKEKT QTLHKFILLF
PIGFVIII   DPPCLTYSYL SHVDLVKDLN SGLIGALLVC REGSLTRERT QNLHEFVLLF
MURFVIII   DPPCLTYSYM SHVDLVKDLN SGLIGALLVC KEGSLSKERT QMLYQFVLLF
CANFVIII   DPPCLTYSYF SHVDLVKDLN SGLIGALLVC KEGSLAKERT QTLQEFVLLF 201                                                 250
HUMFVIII   AVFDEGKSWH SETKNSLMQD RDAASARAWP KMHTVNGYVN RSLPGLIGCH
PIGFVIII   AVFDEGKSWH SARNDSWTRA MDPAPARAQP AMIITVNGYVN RSLPGLIGCH
MURFVIII   AVFDEGKSWH SETNDSYTQS MDSASARDWP KMHTVNGYVN RSLPGLIGCH
CANFVIII   AVFDEGKSWH SETNASLTQ. .....AEAQH ELHTINGYVN RSLPGLTVCH 251                                                 300
HUMFVIII   RKSVYWHVIG MGTTPEVHSI FLEGHTFLVR NHRQASLEIS PITFLTAQTL
PIGFVIII   KKSVYWHVIG MGTSPEVHSI FLEGHTFLVR HHRQASLEIS PLTFLTAQTF
MURFVIII   RKSVYWHVIG MGTTPEIHSI FLEGHTFFVR NHRQASLEIS PITFLTAQTL
CANFVIII   KRSVYWHVIG MGTTPEVHSI FLEGHTFLVR NHRQASLEIS PITFLTAQTF 301                                                 350
HUMFVIII   LMDLGQFLLF CHISSHQHDG MEAYVKVDSC PEEPQLRMK. NNEEAEDYDD
PIGFVIII   LMDLGQFLLF CHISSHHHGG MEAHVRVESC AEEPQLRRK. ADEE.EDYDD
MURFVIII   LIDLGQFLLF CHISSHKHDG MEAYVKVDSC PEESQWQKKN NNEEMEDYDD
CANFVIII   LMDLGQFLLF CHIPSHQHDG MEAYVKVDSC PEEPQLRMK. NNED.KDYDD 351                                                 400
HUMFVIII   DLTDSEMDVV RFDDDNSPSF IQIRSVAKKH PKTWVHYIAA EEEDWDYAPL
PIGFVIII   NLYDSDMDVV RLDGDDVSPF IQIRSVAKKH PKTWVHYISA EEEDWDYAPA
MURFVIII   DLY.SEMDMF TLDYD.SSPF IQIRSVAKKY PKTWIHYISA EEEDWDYAPS
CANFVIII   GLYDSDMDVV SFDDDSSSPF IQIRSVAKKH PKTWVHYIAA EEEDWDYAPS 401                                                 450
HUMFVIII   VLAPDDRSYK SQYLNNGPQR IGRKYKKVRF MAYTDETFKT REAIQHESGI
PIGFVIII   VPSPSDRSYK SLYLNSGPQR IGRKYKKARF VAYTDVTFKT RKAIPYESGI
MURFVIII   VPTSDNGSYK SQYLSNGPHR IGRKYKKVRF IAYTDETFKT RETIQHESGL
CANFVIII   GPTPNDRSHK NLYLNNGPQR IGKKYKKVRF VAYTDETFKT REAIQYESGI 451                                                 500
HUMFVIII   LGPLLYGEVG DTLLIIFKNQ ASRPYNIYPH GITDVRPLYS RRLPKGVKHL
PIGFVIII   LGPLLYGEVG DTLLIIFKNK ASRPYNIYPH GITDVSALHP GRLLKGWKHL
MURFVIII   LGPLLYGEVG DTLLIIFKNQ ASRPYNIYPH GITDVSPLHA RRLPRGIKHV
CANFVIII   LGPLLYGEVG DTLLIIFKNQ ASRPYNIYPH GINYVTPLHT GRLPKGVKHL 501                                                 550
```

Fig. 2a

```
HUMFVIII   KDFPILPGEI FKYKWTVTVE DGPTKSDPRC LTRYYSSFVN MERDLASGLI
PIGFVIII   KDMPILPGET FKYKWTVTVE DGPTKSDPRC LTRYYSSSIN LEKDLASGLI
MURFVIII   KDLPIHPGEI FKYKWTVTVE DGPTKSDPRC LTRYYSSFIN PERDLASGLI
CANFVIII   KDMPILPGEI FKYKWTVTVE DGPTKSDPRC LTRYYSSFIN LERDLASGLI 551                                                600
HUMFVIII   GPLLICYKES VDQRGNQIMS DKRNVILFSV FDENRSWYLT ENIQRFLPNP
PIGFVIII   GPLLICYKES VDQRGNQMMS DKRNVILFSV FDENQSWYLA ENIQRFLPNP
MURFVIII   GPLLICYKES VDQRGNQMMS DKRNVILFSI FDENQSWYIT ENMQRFLPNA
CANFVIII   GPLLICYKES VDQRGNQMMS DKRNVILFSV FDENRSWYLT ENMQRFLPNA 601                                                650
HUMFVIII   AGVQLEDPEF QASNIMHSIN GYVFDSLQLS VCLHEVAYWY ILSIGAQTDF
PIGFVIII   DGLQPQDPEF QASNIMHSIN GYVFDSLQLS VCLHEVAYWY ILSVGAQTDF
MURFVIII   AKTQPQDPGF QASNIMHSIN GYVFDSLELT VCLHEVAYWH ILSVGAQTDF
CANFVIII   DVVQPHDPEF QLSNIMHSIN GYVFDNLQLS VCLHEVAYWY ILSVGAQTDF 651                                                700
HUMFVIII   LSVFFSGYTF KHKMVYEDTL TLFPFSGETV FMSMENPGLW ILGCHNSDFR
PIGFVIII   LSVFFSGYTF KHKMVYEDTL TLFPFSGETV FMSMENPGLW VLGCHNSDLR
MURFVIII   LSIFFSGYTF KHKMVYEDTL TLFPFSGETV FMSMENPGLW VLGCHNSDFR
CANFVIII   LSVFFSGYTF KHKMVYEDTL TLFPFSGETV FMSMENPGLW VLGCHNSDFR 701                                                750
HUMFVIII   NRGMTALLKV SSCDKNTGDY YEDSYEDISA YLLSKNNAIE PRSFSQNSRH
PIGFVIII   NRGMTALLKV YSCDRDIGDY YDNTYEDIPG FLLSGKNVIE PRSFAQNSRP
MURFVIII   KRGMTALLKV SSCDKSTSDY YEEIYEDIPT QLVNENNVID PRSFFQNTNH
CANFVIII   NRGMTALLKV SSCNRNIDDY YEDTYEDIPT PLLNENNVIK PRSFSQNSRH 751                                                800
HUMFVIII   SSTRQKQFNA TTIPENDIEK TDPWFAHRTP MPKIQNVSSS DLLMLLRQS.
PIGFVIII   PSASQKQFQT ITSPEDDVE. LDPQSGERTQ ALEELSVPSG DGSMLLGQN.
MURFVIII   NTRKKKFKD STIPKNDMEK IEPQFEEIAE MLKVQSVSVS DMLMLLGQSH
CANFVIII   STKEKQLKA TTTPENDIEK IDLQSGERTQ LIKAQSVSSS DLLMLLGQN.

801                                                850
HUMFVIII   PTPHGLSLSD LQEAKYETFS DDPSPGAIDS NNSLSEMTHF RPQLHHSGDM
PIGFVIII   PAPHGSSSSD LQEARNE..A DDYLPGARER NTAPSAAARL RPELHHSAER
MURFVIII   PTPHGLFLSD GQEAIYEAIH DDHSPNAIDS NEGPSKVTQL RPESHHSEKI
CANFVIII   PTPRGLFLSD LREA..TDRA DDHSRGAIER NKGPPEVASL RPELRHSEDR 851                                                900
HUMFVIII   VFTPESGLQL RLNEKLGTTA ATELKKLDFK VSSTSNNLI. .STIPSDNLA
PIGFVIII   VLTPEPE... .......... .KELKKLDSK MSSSSDLLKT SPTIPSDTLS
MURFVIII   VFTPQPGLQL RSNKSLETTI EVKWKKLGLQ VSSLPSNLMT .TTILSDNLK
CANFVIII   EFTPEPELQL RLNENLGTNT TVELKKLDLK ISSSSDSLMT SPTIPSDKLA 901                                                950
HUMFVIII   AGTDNTSSLG PPSMPVHYDS QLDTTLFGKK SSPLTESGGP LSLSEENNDS
PIGFVIII   AETERTIISLG PPIIPQVNFRS QLGAIVLGKN SSIIFIGAGVP LGSTEED...
MURFVIII   ATFEKTDSSG FPDMPVHSSS KLSTTAFGKK AYSLVGSHVP LNASEENSDS
CANFVIII   AATEKTGSLG PPNMSVHFNS HLGTIVFGNN SSHLIQSGVP LELSEEDNDS 951                                               1000
HUMFVIII   KLLESGLMNS QESSWGKNVS STESGRLFKG KRAHGPALLT KDNALFKVSI
PIGFVIII   .......... HESSLGENVS PVESDGIFEK ERAHGPASLT KDDVLFKVNI
MURFVIII   NILDSTLMYS QESLPRDNIL SIENDRLLRE KRFHGIALLT KDNTLFKDNV
CANFVIII   KLLEAPLMNI QESSLRENVL SMESNRLFKE ERIRGPASLI KDNALFKVNI
```

Fig. 2b

```
            1001                                            1050
HUMFVIII    SLLKTNKTSN NSATNRKTIII DGPSLLIENS PSVWQNI.LE SDTEFKKVTP
PIGFVIII    SLVKTNKARV YLKTNRKIHI DDAALLTENR ASA....... ..........
MURFVIII    SLMKTNKTYN HSTTNEKLHT ESPT.SIENS TTDLQDAILK VNSEIQEVTA
CANFVIII    SSVKTNRAPV NLTTNRKTRV AIPTLLIENS TSVWQDIMLE RNTEFKEVTS 1051                                            1100
HUMFVIII    LIHDRMLMDK NATALRLNHM SNKTTSSKNM EMVQQKKEGP IPPDAQNPDM
PIGFVIII    .....TFMDK NTTASGLNHV SN........ .......... ..........
MURFVIII    LIHDGTLLGK NSTYLRLNHM LNRTTSTKNK DIFHRKDEDP IPQDEENTIM
CANFVIII    LIHNETFMDR NTTALGLNHV SNKTTLSKNV EMAHQKKEDP VPLRAENPDL 1101                                            1150
HUMFVIII    SFFKMLFLPE SARWIQRTHG KNSLNSGQGP SPKQLVSLGP EKSVEGQNFL
PIGFVIII    .......... ...WIKGPLG KNPLSSERGP SPELLTSSGS GKSVKGQSSG
MURFVIII    PFSKMLFLSE SSNWFKKTNG NNSLNSEQEH SPKQLVYLMF KKYVKNQSFL
CANFVIII    SSSKIPFLPD WI....KTHG KNSLSSEQRP SPKQLTSLGS EKSVKDQNFL 1151                                            1200
HUMFVIII    SEKNKVVVGK GEFTKDVGLK EMVFPSSRNL FLTNLDNLHE NNTHNQEKKI
PIGFVIII    QGRIRVAVEE EELSKG...K EMMLPNSELT FLTNSADVQG NDTHSQGKKS
MURFVIII    SEKNKVTVEQ DGFTKNIGLK DMAFPHNMSI FLTTLSNVHE NGRHNQEKNI
CANFVIII    SE.EKVVVGE DEFTKDTELQ E.IFPNNKSI FFANLANVQE NDTYNQEKKS 1201                                            1250
HUMFVIII    QEEIEKKETL IQENVVLPQI HTVTGTKNFM KNLFLLSTRQ NVEGSYDGAY
PIGFVIII    REEMERREKL VQEKVDLPQV YTATGTKNFL RNIFHQSTEP SVEGFDGGSH
MURFVIII    QEEIE.KEAL IEEKVVLPQV HEATGSKNFL KDILILGTRQ NISLYE..VH
CANFVIII    PEEIERKEKL TQENVALPQA HTMIGTKNFL KNLFLLSTKQ NVAGLEEQPY 1251                                            1300
HUMFVIII    APVLQDFRSL NDSTNRTKKH TAHFSKKG.. EEENLEGLGN QTKQIVEKYA
PIGFVIII    APVPQDSRSL NDSAERAETH IAHFSAIR.. EEAPLEAPGN RT........
MURFVIII    VPVLQNITSI NNSTNTVQIH MEHFFKRRKD KETNSEGLVN KTREMVKNY.
CANFVIII    TPILQDTRSL NDSPHSEGIH MANFSKIR.. EEANLEGLGN QTNQMVERFP 1301                                            1350
HUMFVIII    CTTRISPNTS QQNFVTQRSK RALKQFRLPL EETELEKRII VDDTSTQWSK
PIGFVIII    .......GPG PRSAVPRRVK QSLKQIRLPI EEIKPERGVV LNATSTRWS.
MURFVIII    ........PS QKNITTQRSK RALGQFRL.. .......... ....STQWLK
CANFVIII    STTRMSSNAS QH.VITQRGK RSLKQPRLSQ GEIKFERKVI ANDTSTQWSK 1351                                            1400
HUMFVIII    NMKHLTPSTL TQIDYNEKEK GAITQSPLSD CLTRSHSIPQ ANRSPLPIAK
PIGFVIII    .......... .......... .......... .......... ..........
MURFVIII    TINCSTQCII KQIDHSKEMK KFITKSSLSD SSVIK.STTQ TNSSDSHIVK
CANFVIII    NMNYLAQGTL TQIEYNEKEK RAITQSPLSD CSMRNHVTIQ MNDSALPVAK 1401                                            1450
HUMFVIII    VSSFPSIRPI YLTRVLFQDN SSHLPAAS.. ..YRKKDSGV QESSHFLQGA
PIGFVIII    .......... .......... .......... .......... .ESSPILQGA
MURFVIII    TSAFP...PI DLKRSPFQNK FSHVQASSYI YDFKTKSSRI QESNNFLKET
CANFVIII    ESASPSVRHT DLTKIPSQHN SSHLPASACN YTFRERTSGV QEGSHFLQEA 1451                                            1500
HUMFVIII    KKNNLSLAIL TLEMTGDQRE VGSLGTSATN SVTYKKVENT VLPKPDLPKT
PIGFVIII    KRNNLSLPFL TLEMAGGQGK ISALGKSAAG PLASGKLEKA VLSSAGLSEA
MURFVIII    KINNPSLAIL PWNMFIDQGK FTSPGKSNTN SVTYKKRENI IFLKPTLPEE
CANFVIII    KRNNLSLAFV TLGITEGQGK FSSLGKSATN QPMYKKLENT VLLQPGLSET 1501                                            1550
```

Fig. 2c

```
HUMFVIII    SGKVELLPKV  HIYQKDLFPT  ETSNGSPGHL  DLVEGSLLQG  TEGAIKWNEA
PIGFVIII    SGKAEFLPKV  RVHREDLLPQ  KTSNVSCAHG  DLGQEIFLQK  TRGPVNLNKV
MURFVIII    SGKIELLPQV  SIQEEEILPT  ETSHGSPGHL  NLMKEVFLQK  IQGPTKWNKA
CANFVIII    SDKVELLSQV  HVDQEDSFPT  KTSNDSPGHL  DLMGKIFLQK  TQGPVKMNKT 1551                                            1600
HUMFVIII    NRPGKVPFLR  VATESSAKTP  SKLLDPLAWD  NHYGTQIPKE  EWKSQEKSPE
PIGFVIII    NRPG......  ........RTP SKLLGPPM..  ........PK  EWESLEKSPK
MURFVIII    KRHGES..IK  GKTESSKNTR  SKLLNHHAWD  YHYAAQIPKD  MWKSKEKSPE
CANFVIII    NSPGKVPFLK  WATESSEKIP  SKLLGVLAWD  NIIYDTQIPSE EWKSQKKSQT 1601                                            1650
HUMFVIII    KTAFKKKDTI  .LSLNACESN  HAIAAINEGQ  NKPEIEVTWA  KQGRTERLCS
PIGFVIII    STALRTKDII  SLPLDRHESN  HSIAAKNEGQ  AETQREAAWT  KQGGPGRLCA
MURFVIII    IISIKQEDTI  .LSLRPHGNS  HSIGA.NEKQ  NWPQRETTWV  KQGQTQRTCS
CANFVIII    NTAFKRKDTI  .LPLGPCENN  DSTAAINEGQ  DKPQREAMWA  KQGEPGRLCS 1651                                            1700
HUMFVIII    QNPVLKRHQ   REITRTTLQS  DQEEIDYDDT  ISVEMKKEDF  DIYDEDENQS
PIGFVIII    RPVLKRHQ    EDISLPTFQP  EEDKMDYDDI  FSTETKGEDF  DIYGEDENQD
MURFVIII    QIPVLKRHQ   RELS..AFQS  EQEATDYDDA  ITIETI.EDF  DIYSEDIKQG
CANFVIII    QNPVSKIHQ   REITVTTLQP  EEDKFEYDDT  FSIEMKREDF  DIYGDYENQG 1701                                            1750
HUMFVIII    PRSFQKKTRH  YFIAAVERLW  DYGMSSSPHV  LRNRAQSGSV  PQFKKVVFQE
PIGFVIII    PRSFQKRTRH  YFIAAVEQLW  DYGMSESPRA  LRNRAQNGEV  PRFKKVVFRE
MURFVIII    PRSFQQKTRH  YFIAAVERLW  DYGMSTS.HV  LRNRYQSDNV  PQFKKVVFQE
CANFVIII    LRSFQKKTRH  YFIAAVERLW  DYGMSRSPHI  LRNRAQSGDV  QQFKKVVFQE 1751                                            1800
HUMFVIII    FTDGSFTQPL  YRGELNEHLG  LLGPYIRAEV  EDNIMVTFRN  QASRPYSFYS
PIGFVIII    FADGSFTQPS  YRGELNKHLG  LLGPYIRAEV  EDNIMVTFKN  QASRPYSFYS
MURFVIII    FTDGSFSQPL  YRGELNEHLG  LLGPYIRAEV  EDNIMVTFKN  QASRPYSFYS
CANFVIII    FTDGSFTQPL  YRGELNEHLG  LLGPYIRAEV  EDNIVVTFKN  QASRPYSFYS 1801                                            1850
HUMFVIII    SLISYEEDQR  QGAEPRKNFV  KPNETKTYFW  KVQHHMAPTK  DEFDCKAWAY
PIGFVIII    SLISYPDDQE  QGAEPRHNFV  QPNETRTYFW  KVQHHMAPTE  DEFDCKAWAY
MURFVIII    SLISYKEDQ.  RGEEPRRNFV  KPNETKIYFW  KVQHHMAPTE  DEFDCKAWAY
CANFVIII    SLISYDEDEG  QGAEPRRKFV  NPNETKIYFW  KVQHHMAPTK  DEFDCKAWAY 1851                                            1900
HUMFVIII    FSDVDLEKDV  HSGLIGPLLV  CHTNTLNPAH  GRQVTVQEFA  LFFTIFDETK
PIGFVIII    FSDVDLEKDV  HSGLIGPLLI  CRANTLNAAH  GRQVTVQEFA  LFFTIFDETK
MURFVIII    FSDVDLERDM  HSGLIGPLLI  CHANTLNPAH  GRQVSVQEFA  LLFTIFDETK
CANFVIII    FSDVDLEKDV  HSGLIGPLLI  CRSNTLNPAH  GRQVTVQEFA  LVFTIFDETK 1901                                            1950
HUMFVIII    SWYFTENMER  NCRAPCNIQM  EDPTFKENYR  FHAINGYIMD  TLPGLVMAQD
PIGFVIII    SWYFTENVER  NCRAPCHLQM  EDPTLKENYR  FHAINGYVMD  TLPGLVMAQN
MURFVIII    SWYFTENVKR  NCKTPCNFQM  EDPTLKENYR  FHAINGYVMD  TLPGLVMAQD
CANFVIII    SWYFTENLER  NCRAPCNVQK  EDPTLKENFR  FHAINGYVKD  TLPGLVMAQD 1951                                            2000
HUMFVIII    QRIRWYLLSM  GSNENIHSIH  FSGHVFTVRK  KEEYKMALYN  LYPGVFETVE
PIGFVIII    QRIRWYLLSM  GSNENIHSIH  FSGHVFSVRK  KEEYKMAVYN  LYPGVFETVE
MURFVIII    QRIRWYLLSM  GNNENIQSIH  FSGHVFTVRK  KEEYKMAVYN  LYPGVFETLE
CANFVIII    QKVRWYLLSM  GSNENIHSIH  FSGHVFTVRK  KEEYKMAVYN  LYPGVFETVE 2001                                            2050
HUMFVIII    MLPSKAGIWR  VECLIGEHLH  AGMSTLFLVY  SNKCQTPLGM  ASGHIRDFQI
```

Fig. 2d

```
            PIGFVIII  MLPSKVGIWR IECLIGEHLQ AGMSTTFLVY SKECQAPLGM ASGRIRDFQI
            MURFVIII  MIPSRAGIWR VECLIGEHLQ AGMSTLFLVY SKQCQIPLGM ASGSIRDFQI
            CANFVIII  MLPSQVGIWR IECLIGEHLQ AGMSTLFLVY SKKCQTPLGM ASGHIRDFQI 2051                                            2100
            HUMFVIII  TASGQYGQWA PKLARLHYSG SINAWSTKEP FSWIKVDLLA PMIIHGIKTQ
            PIGFVIII  TASGQYGQWA PKLARLHYSG SINAWSTKDP HSWIKVDLLA PMIIHGIMTQ
            MURFVIII  TASGHYGQWA PNLARLHYSG SINAWSTKEP FSWIKVDLLA PMIVHGIKTQ
            CANFVIII  TASGQYGQWA PKLARLHYSG SINAWSTKDP FSWIKVDLLA PMIIHGIMTQ 2101                                            2150
            HUMFVIII  GARQKFSSLY ISQFIIMYSL DGKKWQTYRG NSTGTLMVFF GNVDSSGIKH
            PIGFVIII  GARQKFSSLY ISQFIIMYSL DGRNWQSYRG NSTGTLMVFF GNVDASGIKH
            MURFVIII  GARQKFSSLY ISQFIIMYSL DGKKWLSYQG NSTGTLMVFF GNVDSSGIKH
            CANFVIII  GARQKFSSLY VSQFIIMYSL DGNKWHSYRG NSTGTLMVFF GNVDSSGIKH 2151                                            2200
            HUMFVIII  NIFNPPIIAR YIRLHPTHYS IRSTLRMELM GCDLNSCSMP LGMESKAISD
            PIGFVIII  NIFNPPIVAR YIRLHPTHYS IRSTLRMELM GCDLNSCSMP LGMQNKAISD
            MURFVIII  NSFNPPIIAR YIRLHPTHSS IRSTLRMELM GCDLNSCSIP LGMESKVISD
            CANFVIII  NIFNPPIIAQ YIRLHPTHYS IRSTLRMELL GCDFNSCSMP LGMESKAISD 2201                                            2250
            HUMFVIII  AQITASSYFT NMFATWSPSK ARLHLQGRSN AWRPQVNNPK EWLQVDFQKT
            PIGFVIII  SQITASSHLS NIFATWSPSQ ARLHLQGRTN AWRPRVSSAE EWLQVDLQKT
            MURFVIII  TQITASSYFT NMFATWSPSQ ARLHLQGRTN AWRPQVNDPK QWLQVDLQKT
            CANFVIII  AQITASSYLS SMLATWSPSQ ARLHLQGRTN AWRPQANNPK EWLQVDFRKT 2251                                            2300
            HUMFVIII  MKVTGVTTQG VKSLLTSMYV KEFLISSSQD GHQWTLFFQN GKVKVFQGNQ
            PIGFVIII  VKVTGITTQG VKSLLSSMYV KEFLVSSSQD GRRWTLFLQD GHTKVFQGNQ
            MURFVIII  MKVTGIITQG VKSLFTSMFV KEFLISSSQD GHHWTQILYN GKVKVFQGNQ
            CANFVIII  MKVTGITTQG VKSLLISMYV KEFLISSSQD GHNWTLFLQN GKVKVFQGNR 2301                                       2345
            HUMFVIII  DSFTPVVNSL DPPLLTRYLR IHPQSWVHQI ALRMEVLGCE AQDLY
            PIGFVIII  DSSTPVVNAL DPPLFTRYLR IHPTSWAQHI ALRLEVLGCE AQDLY
            MURFVIII  DSSTPMMNSL DPPLLTRYLR IHPQIWEHQI ALRLEILGCE AQQQY
            CANFVIII  DSSTPVRNRL EPPLVARYVR LHPQSWAHHI ALRLEVLGCD TQQPA
```

Fig. 2e

SEQUENCE LISTING

<160> NUMBER OF SEQ ID NOS: 12

<210> SEQ ID NO 1
<211> LENGTH: 1421
<212> TYPE: PRT
<213> ORGANISM: sus scrofa

<400> SEQUENCE: 1

```
Ala Ile Arg Arg Tyr Tyr Leu Gly Ala Val Glu Leu Ser Trp Asp Tyr
1               5                   10                  15

Arg Gln Ser Glu Leu Leu Arg Glu Leu His Val Asp Thr Arg Phe Pro
            20                  25                  30

Ala Thr Ala Pro Gly Ala Leu Pro Leu Gly Pro Ser Val Leu Tyr Lys
        35                  40                  45

Lys Thr Val Phe Val Glu Phe Thr Asp Gln Leu Phe Ser Val Ala Arg
    50                  55                  60

Pro Arg Pro Pro Trp Met Gly Leu Leu Gly Pro Thr Ile Gln Ala Glu
65                  70                  75                  80

Val Tyr Asp Thr Val Val Thr Leu Lys Asn Met Ala Ser His Pro
                85                  90                  95

Val Ser Leu His Ala Val Gly Val Ser Phe Trp Lys Ser Ser Glu Gly
                100                 105                 110

Ala Glu Tyr Glu Asp His Thr Ser Gln Arg Glu Lys Glu Asp Asp Lys
            115                 120                 125

Val Leu Pro Gly Lys Ser Gln Thr Tyr Val Trp Gln Val Leu Lys Glu
        130                 135                 140

Asn Gly Pro Thr Ala Ser Asp Pro Pro Cys Leu Thr Tyr Ser Tyr Leu
145                 150                 155                 160

Ser His Val Asp Leu Val Lys Asp Leu Asn Ser Gly Leu Ile Gly Ala
                165                 170                 175

Leu Leu Val Cys Arg Glu Gly Ser Leu Thr Arg Glu Thr Gln Asn
            180                 185                 190

Leu His Glu Phe Val Leu Leu Phe Ala Val Phe Asp Glu Gly Lys Ser
        195                 200                 205

Trp His Ser Ala Arg Asn Asp Ser Trp Thr Arg Ala Met Asp Pro Ala
    210                 215                 220

Pro Ala Arg Ala Gln Pro Ala Met His Thr Val Asn Gly Tyr Val Asn
225                 230                 235                 240

Arg Ser Leu Pro Gly Leu Ile Gly Cys His Lys Lys Ser Val Tyr Trp
                245                 250                 255

His Val Ile Gly Met Gly Thr Ser Pro Glu Val His Ser Ile Phe Leu
                260                 265                 270

Glu Gly His Thr Phe Leu Val Arg His His Arg Gln Ala Ser Leu Glu
            275                 280                 285

Ile Ser Pro Leu Thr Phe Leu Thr Ala Gln Thr Phe Leu Met Asp Leu
        290                 295                 300

Gly Gln Phe Leu Leu Phe Cys His Ile Ser Ser His His Gly Gly
305                 310                 315                 320

Met Glu Ala His Val Arg Val Glu Ser Cys Ala Glu Pro Gln Leu
                325                 330                 335

Arg Arg Lys Ala Asp Glu Glu Glu Asp Tyr Asp Asp Asn Leu Tyr Asp
            340                 345                 350

Ser Asp Met Asp Val Val Arg Leu Asp Gly Asp Val Ser Pro Phe
        355                 360                 365
```

-continued

```
Ile Gln Ile Arg Ser Val Ala Lys Lys His Pro Lys Thr Trp Val His
370                 375                 380

Tyr Ile Ser Ala Glu Glu Asp Trp Asp Tyr Ala Pro Ala Val Pro
385                 390                 395                 400

Ser Pro Ser Asp Arg Ser Tyr Lys Ser Leu Tyr Leu Asn Ser Gly Pro
            405                 410                 415

Gln Arg Ile Gly Arg Lys Tyr Lys Ala Arg Phe Val Ala Tyr Thr
        420                 425                 430

Asp Val Thr Phe Lys Thr Arg Lys Ala Ile Pro Tyr Glu Ser Gly Ile
            435                 440                 445

Leu Gly Pro Leu Leu Tyr Gly Glu Val Gly Asp Thr Leu Leu Ile Ile
450                 455                 460

Phe Lys Asn Lys Ala Ser Arg Pro Tyr Asn Ile Tyr Pro His Gly Ile
465                 470                 475                 480

Thr Asp Val Ser Ala Leu His Pro Gly Arg Leu Leu Lys Gly Trp Lys
            485                 490                 495

His Leu Lys Asp Met Pro Ile Leu Pro Gly Glu Thr Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Ile Asn Leu Glu Lys Asp Leu Ala
530                 535                 540

Ser Gly Leu Ile Gly Pro Leu Leu Ile Cys Tyr Lys Glu Ser Val Asp
545                 550                 555                 560

Gln Arg Gly Asn Gln Met Met Ser Asp Lys Arg Asn Val Ile Leu Phe
            565                 570                 575

Ser Val Phe Asp Glu Asn Gln Ser Trp Tyr Leu Ala Glu Asn Ile Gln
            580                 585                 590

Arg Phe Leu Pro Asn Pro Asp Gly Leu Gln Pro Gln Asp Pro Glu Phe
        595                 600                 605

Gln Ala Ser Asn Ile Met His Ser Ile Asn Gly Tyr Val Phe Asp Ser
            610                 615                 620

Leu Gln Leu Ser Val Cys Leu His Glu Val Ala Tyr Trp Tyr Ile Leu
625                 630                 635                 640

Ser Val Gly Ala Gln Thr Asp Phe Leu Ser Val Phe Phe Ser Gly Tyr
            645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Val Leu Gly Cys His Asn Ser Asp Leu Arg Asn Arg Gly Met Thr Ala
        690                 695                 700

Leu Leu Lys Val Tyr Ser Cys Asp Arg Ser Phe Ala Gln Asn Ser Arg
705                 710                 715                 720

Pro Pro Ser Ala Ser Ala Pro Lys Pro Pro Val Leu Arg Arg His Gln
            725                 730                 735

Arg Asp Ile Ser Leu Pro Thr Phe Gln Pro Glu Glu Asp Lys Met Asp
        740                 745                 750

Tyr Asp Asp Ile Phe Ser Thr Glu Thr Lys Gly Glu Asp Phe Asp Ile
            755                 760                 765

Tyr Gly Glu Asp Glu Asn Gln Asp Pro Arg Ser Phe Gln Lys Arg Thr
770                 775                 780

Arg His Tyr Phe Ile Ala Ala Val Glu Gln Leu Trp Asp Tyr Gly Met
```

-continued

```
785                 790                 795                 800
Ser Glu Ser Pro Arg Ala Leu Arg Asn Arg Ala Gln Asn Gly Glu Val
            805                 810                 815

Pro Arg Phe Lys Lys Val Val Phe Arg Glu Phe Ala Asp Gly Ser Phe
            820                 825                 830

Thr Gln Pro Ser Tyr Arg Gly Glu Leu Asn Lys His Leu Gly Leu Leu
            835                 840                 845

Gly Pro Tyr Ile Arg Ala Glu Val Asp Asn Ile Met Val Thr Phe
850                 855                 860

Lys Asn Gln Ala Ser Arg Pro Tyr Ser Phe Tyr Ser Ser Leu Ile Ser
865                 870                 875                 880

Tyr Pro Asp Asp Gln Glu Gln Gly Ala Glu Pro Arg His Asn Phe Val
            885                 890                 895

Gln Pro Asn Glu Thr Arg Thr Tyr Phe Trp Lys Val Gln His His Met
            900                 905                 910

Ala Pro Thr Glu Asp Glu Phe Asp Cys Lys Ala Trp Ala Tyr Phe Ser
            915                 920                 925

Asp Val Asp Leu Glu Lys Asp Val His Ser Gly Leu Ile Gly Pro Leu
930                 935                 940

Leu Ile Cys Arg Ala Asn Thr Leu Asn Ala Ala His Gly Arg Gln Val
945                 950                 955                 960

Thr Val Gln Glu Phe Ala Leu Phe Phe Thr Ile Phe Asp Glu Thr Lys
            965                 970                 975

Ser Trp Tyr Phe Thr Glu Asn Val Glu Arg Asn Cys Arg Ala Pro Cys
            980                 985                 990

His Leu Gln Met Glu Asp Pro Thr Leu Lys Glu Asn Tyr Arg Phe His
    995                 1000                1005

Ala Ile Asn Gly Tyr Val Met Asp Thr Leu Pro Gly Leu Val Met
    1010                1015                1020

Ala Gln Asn Gln Arg Ile Arg Trp Tyr Leu Leu Ser Met Gly Ser
    1025                1030                1035

Asn Glu Asn Ile His Ser Ile His Phe Ser Gly His Val Phe Ser
    1040                1045                1050

Val Arg Lys Lys Glu Glu Tyr Lys Met Ala Val Tyr Asn Leu Tyr
    1055                1060                1065

Pro Gly Val Phe Glu Thr Val Glu Met Leu Pro Ser Lys Val Gly
    1070                1075                1080

Ile Trp Arg Ile Glu Cys Leu Ile Gly Glu His Leu Gln Ala Gly
    1085                1090                1095

Met Ser Thr Thr Phe Leu Val Tyr Ser Lys Glu Cys Gln Ala Pro
    1100                1105                1110

Leu Gly Met Ala Ser Gly Arg Ile Arg Asp Phe Gln Ile Thr Ala
    1115                1120                1125

Ser Gly Gln Tyr Gly Gln Trp Ala Pro Lys Leu Ala Arg Leu His
    1130                1135                1140

Tyr Ser Gly Ser Ile Asn Ala Trp Ser Thr Lys Asp Pro His Ser
    1145                1150                1155

Trp Ile Lys Val Asp Leu Leu Ala Pro Met Ile Ile His Gly Ile
    1160                1165                1170

Met Thr Gln Gly Ala Arg Gln Lys Phe Ser Ser Leu Tyr Ile Ser
    1175                1180                1185

Gln Phe Ile Ile Met Tyr Ser Leu Asp Gly Arg Asn Trp Gln Ser
    1190                1195                1200
```

```
Tyr Arg Gly Asn Ser Thr Gly Thr Leu Met Val Phe Phe Gly Asn
    1205                1210                1215

Val Asp Ala Ser Gly Ile Lys His Asn Ile Phe Asn Pro Pro Ile
    1220                1225                1230

Val Ala Arg Tyr Ile Arg Leu His Pro Thr His Tyr Ser Ile Arg
    1235                1240                1245

Ser Thr Leu Arg Met Glu Leu Met Gly Cys Asp Leu Asn Ser Cys
    1250                1255                1260

Ser Met Pro Leu Gly Met Gln Asn Lys Ala Ile Ser Asp Ser Gln
    1265                1270                1275

Ile Thr Ala Ser Ser His Leu Ser Asn Ile Phe Ala Thr Trp Ser
    1280                1285                1290

Pro Ser Gln Ala Arg Leu His Leu Gln Gly Arg Thr Asn Ala Trp
    1295                1300                1305

Arg Pro Arg Val Ser Ser Ala Glu Glu Trp Leu Gln Val Asp Leu
    1310                1315                1320

Gln Lys Thr Val Lys Val Thr Gly Ile Thr Thr Gln Gly Val Lys
    1325                1330                1335

Ser Leu Leu Ser Ser Met Tyr Val Lys Glu Phe Leu Val Ser Ser
    1340                1345                1350

Ser Gln Asp Gly Arg Arg Trp Thr Leu Phe Leu Gln Asp Gly His
    1355                1360                1365

Thr Lys Val Phe Gln Gly Asn Gln Asp Ser Ser Thr Pro Val Val
    1370                1375                1380

Asn Ala Leu Asp Pro Pro Leu Phe Thr Arg Tyr Leu Arg Ile His
    1385                1390                1395

Pro Thr Ser Trp Ala Gln His Ile Ala Leu Arg Leu Glu Val Leu
    1400                1405                1410

Gly Cys Glu Ala Gln Asp Leu Tyr
    1415                1420

<210> SEQ ID NO 2
<211> LENGTH: 1397
<212> TYPE: PRT
<213> ORGANISM: homo sapiens

<400> SEQUENCE: 2

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
                20                  25                  30

Arg Val Pro Lys Ser Phe Pro Phe Asn Thr Ser Val Val Tyr Lys Lys
            35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
            115                 120                 125

Phe Pro Gly Gly Ser His Thr Tyr Val Trp Gln Val Leu Lys Glu Asn
```

```
            130                 135                 140
Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560
```

-continued

```
Gln Arg Gly Asn Gln Ile Met Ser Asp Lys Arg Asn Val Ile Leu Phe
            565                 570                 575
Ser Val Phe Asp Glu Asn Arg Ser Trp Tyr Leu Thr Glu Asn Ile Gln
            580                 585                 590
Arg Phe Leu Pro Asn Pro Ala Gly Val Gln Leu Glu Asp Pro Glu Phe
            595                 600                 605
Gln Ala Ser Asn Ile Met His Ser Ile Asn Gly Tyr Val Phe Asp Ser
            610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
            645                 650                 655
Thr Phe Lys His Lys Met Val Tyr Glu Asp Thr Leu Thr Leu Phe Pro
            660                 665                 670
Phe Ser Gly Glu Thr Val Phe Met Ser Met Glu Asn Pro Gly Leu Trp
            675                 680                 685
Ile Leu Gly Cys His Asn Ser Asp Phe Arg Asn Arg Gly Met Thr Ala
            690                 695                 700
Leu Leu Lys Val Ser Ser Cys Asp Lys Glu Ile Thr Arg Thr Thr Leu
705                 710                 715                 720
Gln Ser Asp Gln Glu Glu Ile Asp Tyr Asp Asp Thr Ile Ser Val Glu
            725                 730                 735
Met Lys Lys Glu Asp Phe Asp Ile Tyr Asp Glu Asp Glu Asn Gln Ser
            740                 745                 750
Pro Arg Ser Phe Gln Lys Lys Thr Arg His Tyr Phe Ile Ala Ala Val
            755                 760                 765
Glu Arg Leu Trp Asp Tyr Gly Met Ser Ser Ser Pro His Val Leu Arg
            770                 775                 780
Asn Arg Ala Gln Ser Gly Ser Val Pro Gln Phe Lys Lys Val Val Phe
785                 790                 795                 800
Gln Glu Phe Thr Asp Gly Ser Phe Thr Gln Pro Leu Tyr Arg Gly Glu
            805                 810                 815
Leu Asn Glu His Leu Gly Leu Leu Gly Pro Tyr Ile Arg Ala Glu Val
            820                 825                 830
Glu Asp Asn Ile Met Val Thr Phe Arg Asn Gln Ala Ser Arg Pro Tyr
            835                 840                 845
Ser Phe Tyr Ser Ser Leu Ile Ser Tyr Glu Glu Asp Gln Arg Gln Gly
            850                 855                 860
Ala Glu Pro Arg Lys Asn Phe Val Lys Pro Asn Glu Thr Lys Thr Tyr
865                 870                 875                 880
Phe Trp Lys Val Gln His His Met Ala Pro Thr Lys Asp Glu Phe Asp
            885                 890                 895
Cys Lys Ala Trp Ala Tyr Phe Ser Asp Val Asp Leu Glu Lys Asp Val
            900                 905                 910
His Ser Gly Leu Ile Gly Pro Leu Leu Val Cys His Thr Asn Thr Leu
            915                 920                 925
Asn Pro Ala His Gly Arg Gln Val Thr Val Gln Glu Phe Ala Leu Phe
            930                 935                 940
Phe Thr Ile Phe Asp Glu Thr Lys Ser Trp Tyr Phe Thr Glu Asn Met
945                 950                 955                 960
Glu Arg Asn Cys Arg Ala Pro Cys Asn Ile Gln Met Glu Asp Pro Thr
            965                 970                 975
```

```
Phe Lys Glu Asn Tyr Arg Phe His Ala Ile Asn Gly Tyr Ile Met Asp
            980                 985                 990

Thr Leu Pro Gly Leu Val Met Ala  Gln Asp Gln Arg Ile  Arg Trp Tyr
        995                 1000                1005

Leu Leu Ser Met Gly Ser Asn  Glu Asn Ile His Ser  Ile His Phe
        1010                1015                1020

Ser Gly His Val Phe Thr Val  Arg Lys Lys Glu Glu  Tyr Lys Met
        1025                1030                1035

Ala Leu Tyr Asn Leu Tyr Pro  Gly Val Phe Glu Thr  Val Glu Met
        1040                1045                1050

Leu Pro Ser Lys Ala Gly Ile  Trp Arg Val Glu Cys  Leu Ile Gly
        1055                1060                1065

Glu His Leu His Ala Gly Met  Ser Thr Leu Phe Leu  Val Tyr Ser
        1070                1075                1080

Asn Lys Cys Gln Thr Pro Leu  Gly Met Ala Ser Gly  His Ile Arg
        1085                1090                1095

Asp Phe Gln Ile Thr Ala Ser  Gly Gln Tyr Gly Gln  Trp Ala Pro
        1100                1105                1110

Lys Leu Ala Arg Leu His Tyr  Ser Gly Ser Ile Asn  Ala Trp Ser
        1115                1120                1125

Thr Lys Glu Pro Phe Ser Trp  Ile Lys Val Asp Leu  Leu Ala Pro
        1130                1135                1140

Met Ile Ile His Gly Ile Lys  Thr Gln Gly Ala Arg  Gln Lys Phe
        1145                1150                1155

Ser Ser Leu Tyr Ile Ser Gln  Phe Ile Ile Met Tyr  Ser Leu Asp
        1160                1165                1170

Gly Lys Lys Trp Gln Thr Tyr  Arg Gly Asn Ser Thr  Gly Thr Leu
        1175                1180                1185

Met Val Phe Phe Gly Asn Val  Asp Ser Ser Gly Ile  Lys His Asn
        1190                1195                1200

Ile Phe Asn Pro Pro Ile Ile  Ala Arg Tyr Ile Arg  Leu His Pro
        1205                1210                1215

Thr His Tyr Ser Ile Arg Ser  Thr Leu Arg Met Glu  Leu Met Gly
        1220                1225                1230

Cys Asp Leu Asn Ser Cys Ser  Met Pro Leu Gly Met  Glu Ser Lys
        1235                1240                1245

Ala Ile Ser Asp Ala Gln Ile  Thr Ala Ser Ser Tyr  Phe Thr Asn
        1250                1255                1260

Met Phe Ala Thr Trp Ser Pro  Ser Lys Ala Arg Leu  His Leu Gln
        1265                1270                1275

Gly Arg Ser Asn Ala Trp Arg  Pro Gln Val Asn Asn  Pro Lys Glu
        1280                1285                1290

Trp Leu Gln Val Asp Phe Gln  Lys Thr Met Lys Val  Thr Gly Val
        1295                1300                1305

Thr Thr Gln Gly Val Lys Ser  Leu Leu Thr Ser Met  Tyr Val Lys
        1310                1315                1320

Glu Phe Leu Ile Ser Ser Ser  Gln Asp Gly His Gln  Trp Thr Leu
        1325                1330                1335

Phe Phe Gln Asn Gly Lys Val  Lys Val Phe Gln Gly  Asn Gln Asp
        1340                1345                1350

Ser Phe Thr Pro Val Val Asn  Ser Leu Asp Pro Pro  Leu Leu Thr
        1355                1360                1365

Arg Tyr Leu Arg Ile His Pro  Gln Ser Trp Val His  Gln Ile Ala
```

```
            1370                1375                1380
Leu Arg Met Glu Val Leu Gly Cys Glu Ala Gln Asp Leu Tyr
            1385                1390                1395

<210> SEQ ID NO 3
<211> LENGTH: 1397
<212> TYPE: PRT
<213> ORGANISM: Canis familiaris

<400> SEQUENCE: 3

Ala Thr Arg Lys Tyr Tyr Leu Gly Ala Val Glu Leu Ser Trp Asp Tyr
  1               5                  10                  15

Met Gln Ser Asp Leu Leu Ser Ala Leu His Ala Asp Thr Ser Phe Ser
             20                  25                  30

Ser Arg Val Pro Gly Ser Leu Pro Leu Thr Thr Ser Val Thr Tyr Arg
         35                  40                  45

Lys Thr Val Phe Val Glu Phe Thr Asp Asp Leu Phe Asn Ile Ala Lys
     50                  55                  60

Pro Arg Pro Pro Trp Met Gly Leu Leu Gly Pro Thr Ile Gln Ala Glu
 65                  70                  75                  80

Val Tyr Asp Thr Val Val Ile Val Leu Lys Asn Met Ala Ser His Pro
                 85                  90                  95

Val Ser Leu His Ala Val Gly Val Ser Tyr Trp Lys Ala Ser Glu Gly
            100                 105                 110

Ala Glu Tyr Glu Asp Gln Thr Ser Gln Lys Glu Lys Glu Asp Asp Asn
        115                 120                 125

Val Ile Pro Gly Glu Ser His Thr Tyr Val Trp Gln Val Leu Lys Glu
    130                 135                 140

Asn Gly Pro Met Ala Ser Asp Pro Pro Cys Leu Thr Tyr Ser Tyr Phe
145                 150                 155                 160

Ser His Val Asp Leu Val Lys Asp Leu Asn Ser Gly Leu Ile Gly Ala
                165                 170                 175

Leu Leu Val Cys Lys Glu Gly Ser Leu Ala Lys Glu Arg Thr Gln Thr
            180                 185                 190

Leu Gln Glu Phe Val Leu Leu Phe Ala Val Phe Asp Glu Gly Lys Ser
        195                 200                 205

Trp His Ser Glu Thr Asn Ala Ser Leu Thr Gln Ala Glu Ala Gln His
    210                 215                 220

Glu Leu His Thr Ile Asn Gly Tyr Val Asn Arg Ser Leu Pro Gly Leu
225                 230                 235                 240

Thr Val Cys His Lys Arg Ser Val Tyr Trp His Val Ile Gly Met Gly
                245                 250                 255

Thr Thr Pro Glu Val His Ser Ile Phe Leu Glu Gly His Thr Phe Leu
            260                 265                 270

Val Arg Asn His Arg Gln Ala Ser Leu Glu Ile Ser Pro Ile Thr Phe
        275                 280                 285

Leu Thr Ala Gln Thr Phe Leu Met Asp Leu Gly Gln Phe Leu Leu Phe
    290                 295                 300

Cys His Ile Pro Ser His Gln His Asp Gly Met Glu Ala Tyr Val Lys
305                 310                 315                 320

Val Asp Ser Cys Pro Glu Glu Pro Gln Leu Arg Met Lys Asn Asn Glu
                325                 330                 335

Asp Lys Asp Tyr Asp Asp Gly Leu Tyr Asp Ser Asp Met Asp Val Val
            340                 345                 350
```

-continued

```
Ser Phe Asp Asp Ser Ser Pro Phe Ile Gln Ile Arg Ser Val
            355                 360             365

Ala Lys Lys His Pro Lys Thr Trp Val His Tyr Ile Ala Ala Glu Glu
370                 375                 380

Glu Asp Trp Asp Tyr Ala Pro Ser Gly Pro Thr Pro Asn Asp Arg Ser
385                 390                 395                 400

His Lys Asn Leu Tyr Leu Asn Asn Gly Pro Gln Arg Ile Gly Lys Lys
                405                 410                 415

Tyr Lys Lys Val Arg Phe Val Ala Tyr Thr Asp Glu Thr Phe Lys Thr
                420                 425                 430

Arg Glu Ala Ile Gln Tyr Glu Ser Gly Ile Leu Gly Pro Leu Leu Tyr
            435                 440                 445

Gly Glu Val Gly Asp Thr Leu Leu Ile Ile Phe Lys Asn Gln Ala Ser
450                 455                 460

Arg Pro Tyr Asn Ile Tyr Pro His Gly Ile Asn Tyr Val Thr Pro Leu
465                 470                 475                 480

His Thr Gly Arg Leu Pro Lys Gly Val Lys His Leu Lys Asp Met Pro
                485                 490                 495

Ile Leu Pro Gly Glu Ile Phe Lys Tyr Lys Trp Thr Val Thr Val Glu
                500                 505                 510

Asp Gly Pro Thr Lys Ser Asp Pro Arg Cys Leu Thr Arg Tyr Tyr Ser
            515                 520                 525

Ser Phe Ile Asn Leu Glu Arg Asp Leu Ala Ser Gly Leu Ile Gly Pro
            530                 535                 540

Leu Leu Ile Cys Tyr Lys Glu Ser Val Asp Gln Arg Gly Asn Gln Met
545                 550                 555                 560

Met Ser Asp Lys Arg Asn Val Ile Leu Phe Ser Val Phe Asp Glu Asn
                565                 570                 575

Arg Ser Trp Tyr Leu Thr Glu Asn Met Gln Arg Phe Leu Pro Asn Ala
                580                 585                 590

Asp Val Val Gln Pro His Asp Pro Glu Phe Gln Leu Ser Asn Ile Met
            595                 600                 605

His Ser Ile Asn Gly Tyr Val Phe Asp Asn Leu Gln Leu Ser Val Cys
610                 615                 620

Leu His Glu Val Ala Tyr Trp Tyr Ile Leu Ser Val Gly Ala Gln Thr
625                 630                 635                 640

Asp Phe Leu Ser Val Phe Phe Ser Gly Tyr Thr Phe Lys His Lys Met
                645                 650                 655

Val Tyr Glu Asp Thr Leu Thr Leu Phe Pro Phe Ser Gly Glu Thr Val
                660                 665                 670

Phe Met Ser Met Glu Asn Pro Gly Leu Trp Val Leu Gly Cys His Asn
            675                 680                 685

Ser Asp Phe Arg Asn Phe Val Ile Ile Asn Arg Gly Met Thr Ala
            690                 695                 700

Leu Leu Lys Val Ser Ser Cys Asn Arg Glu Ile Thr Val Thr Thr Leu
705                 710                 715                 720

Gln Pro Glu Glu Asp Lys Phe Glu Tyr Asp Asp Thr Phe Ser Ile Glu
                725                 730                 735

Met Lys Arg Glu Asp Phe Asp Ile Tyr Gly Asp Tyr Glu Asn Gln Gly
                740                 745                 750

Leu Arg Ser Phe Gln Lys Lys Thr Arg His Tyr Phe Ile Ala Ala Val
            755                 760                 765

Glu Arg Leu Trp Asp Tyr Gly Met Ser Arg Ser Pro His Ile Leu Arg
```

```
                    770                 775                 780
Asn Arg Ala Gln Ser Gly Asp Val Gln Gln Phe Lys Lys Val Val Phe
785                 790                 795                 800

Gln Glu Phe Thr Asp Gly Ser Phe Thr Gln Pro Leu Tyr Arg Gly Glu
                    805                 810                 815

Leu Asn Glu His Leu Gly Leu Leu Gly Pro Tyr Ile Arg Ala Glu Val
                    820                 825                 830

Glu Asp Asn Ile Val Val Thr Phe Lys Asn Gln Ala Ser Arg Pro Tyr
                    835                 840                 845

Ser Phe Tyr Ser Ser Leu Ile Ser Tyr Asp Glu Asp Glu Gly Gln Gly
850                 855                 860

Ala Glu Pro Arg Arg Lys Phe Val Asn Pro Asn Glu Thr Lys Ile Tyr
865                 870                 875                 880

Phe Trp Lys Val Gln His His Met Ala Pro Thr Lys Asp Glu Phe Asp
                    885                 890                 895

Cys Lys Ala Trp Ala Tyr Phe Ser Asp Val Asp Leu Glu Lys Asp Val
                    900                 905                 910

His Ser Gly Leu Ile Gly Pro Leu Leu Ile Cys Arg Ser Asn Thr Leu
                    915                 920                 925

Asn Pro Ala His Gly Arg Gln Val Thr Val Gln Glu Phe Ala Leu Val
930                 935                 940

Phe Thr Ile Phe Asp Glu Thr Lys Ser Trp Tyr Phe Thr Glu Asn Leu
945                 950                 955                 960

Glu Arg Asn Cys Arg Ala Pro Cys Asn Val Gln Lys Glu Asp Pro Thr
                    965                 970                 975

Leu Lys Glu Asn Phe Arg Phe His Ala Ile Asn Gly Tyr Val Lys Asp
                    980                 985                 990

Thr Leu Pro Gly Leu Val Met Ala Gln Asp Gln Lys Val Arg Trp Tyr
                    995                1000                1005

Leu Leu Ser Met Gly Ser Asn Glu Asn Ile His Ser Ile His Phe
1010                1015                1020

Ser Gly His Val Phe Thr Val Arg Lys Lys Glu Glu Tyr Lys Met
1025                1030                1035

Ala Val Tyr Asn Leu Tyr Pro Gly Val Phe Glu Thr Val Glu Met
1040                1045                1050

Leu Pro Ser Gln Val Gly Ile Trp Arg Ile Glu Cys Leu Ile Gly
1055                1060                1065

Glu His Leu Gln Ala Gly Met Ser Thr Leu Phe Leu Val Tyr Ser
1070                1075                1080

Lys Lys Cys Gln Thr Pro Leu Gly Met Ala Ser Gly His Ile Arg
1085                1090                1095

Asp Phe Gln Ile Thr Ala Ser Gly Gln Tyr Gly Gln Trp Ala Pro
1100                1105                1110

Lys Leu Ala Arg Leu His Tyr Ser Gly Ser Ile Asn Ala Trp Ser
1115                1120                1125

Thr Lys Asp Pro Phe Ser Trp Ile Lys Val Asp Leu Leu Ala Pro
1130                1135                1140

Met Ile Ile His Gly Ile Met Thr Gln Gly Ala Arg Gln Lys Phe
1145                1150                1155

Ser Ser Leu Tyr Val Ser Gln Phe Ile Ile Met Tyr Ser Leu Asp
1160                1165                1170

Gly Asn Lys Trp His Ser Tyr Arg Gly Asn Ser Thr Gly Thr Leu
1175                1180                1185
```

```
Met Val Phe Phe Gly Asn Val Asp Ser Ser Gly Ile Lys His Asn
    1190            1195                1200
Ile Phe Asn Pro Pro Ile Ile Ala Gln Tyr Ile Arg Leu His Pro
    1205            1210                1215
Thr His Tyr Ser Ile Arg Ser Thr Leu Arg Met Glu Leu Leu Gly
    1220            1225                1230
Cys Asp Phe Asn Ser Cys Ser Met Pro Leu Gly Met Glu Ser Lys
    1235            1240                1245
Ala Ile Ser Asp Ala Gln Ile Thr Ala Ser Ser Tyr Leu Ser Ser
    1250            1255                1260
Met Leu Ala Thr Trp Ser Pro Ser Gln Ala Arg Leu His Leu Gln
    1265            1270                1275
Gly Arg Thr Asn Ala Trp Arg Pro Gln Ala Asn Asn Pro Lys Glu
    1280            1285                1290
Trp Leu Gln Val Asp Phe Arg Lys Thr Met Lys Val Thr Gly Ile
    1295            1300                1305
Thr Thr Gln Gly Val Lys Ser Leu Leu Ile Ser Met Tyr Val Lys
    1310            1315                1320
Glu Phe Leu Ile Ser Ser Ser Gln Asp Gly His Asn Trp Thr Leu
    1325            1330                1335
Phe Leu Gln Asn Gly Lys Val Lys Val Phe Gln Gly Asn Arg Asp
    1340            1345                1350
Ser Ser Thr Pro Val Arg Asn Arg Leu Glu Pro Pro Leu Val Ala
    1355            1360                1365
Arg Tyr Val Arg Leu His Pro Gln Ser Trp Ala His His Ile Ala
    1370            1375                1380
Leu Arg Leu Glu Val Leu Gly Cys Asp Thr Gln Gln Pro Ala
    1385            1390                1395

<210> SEQ ID NO 4
<211> LENGTH: 24
<212> TYPE: PRT
<213> ORGANISM: sus scrofa

<400> SEQUENCE: 4

Ser Phe Ala Gln Asn Ser Arg Pro Pro Ser Ala Ser Ala Pro Lys Pro
1               5                   10                  15

Pro Val Leu Arg Arg His Gln Arg
            20

<210> SEQ ID NO 5
<211> LENGTH: 24
<212> TYPE: PRT
<213> ORGANISM: homo sapiens

<400> SEQUENCE: 5

Ser Phe Ser Gln Asn Ser Arg His Pro Ser Thr Arg Ser Gln Asn Pro
1               5                   10                  15

Pro Val Leu Lys Arg His Gln Arg
            20

<210> SEQ ID NO 6
<211> LENGTH: 24
<212> TYPE: PRT
<213> ORGANISM: Canis familiaris

<400> SEQUENCE: 6
```

```
Ser Phe Ser Gln Asn Ser Arg His Pro Ser Thr Lys Ser Gln Asn Pro
1               5                   10                  15

Pro Val Ser Lys His His Gln Arg
            20
```

<210> SEQ ID NO 7
<211> LENGTH: 2114
<212> TYPE: PRT
<213> ORGANISM: Sus scrofa

<400> SEQUENCE: 7

```
Ala Ile Arg Arg Tyr Tyr Leu Gly Ala Val Glu Leu Ser Trp Asp Tyr
1               5                   10                  15

Arg Gln Ser Glu Leu Leu Arg Glu Leu His Val Asp Thr Arg Phe Pro
                20                  25                  30

Ala Thr Ala Pro Gly Ala Leu Pro Leu Gly Pro Ser Val Leu Tyr Lys
            35                  40                  45

Lys Thr Val Phe Val Glu Phe Thr Asp Gln Leu Phe Ser Val Ala Arg
    50                  55                  60

Pro Arg Pro Pro Trp Met Gly Leu Leu Gly Pro Thr Ile Gln Ala Glu
65                  70                  75                  80

Val Tyr Asp Thr Val Val Thr Leu Lys Asn Met Ala Ser His Pro
                85                  90                  95

Val Ser Leu His Ala Val Gly Val Ser Phe Trp Lys Ser Glu Gly
                100                 105                 110

Ala Glu Tyr Glu Asp His Thr Ser Gln Arg Glu Lys Glu Asp Asp Lys
                115                 120                 125

Val Leu Pro Gly Lys Ser Gln Thr Tyr Val Trp Gln Val Leu Lys Glu
    130                 135                 140

Asn Gly Pro Thr Ala Ser Asp Pro Pro Cys Leu Thr Tyr Ser Tyr Leu
145                 150                 155                 160

Ser His Val Asp Leu Val Lys Asp Leu Asn Ser Gly Leu Ile Gly Ala
                165                 170                 175

Leu Leu Val Cys Arg Glu Gly Ser Leu Thr Arg Glu Arg Thr Gln Asn
                180                 185                 190

Leu His Glu Phe Val Leu Leu Phe Ala Val Phe Asp Glu Gly Lys Ser
            195                 200                 205

Trp His Ser Ala Arg Asn Asp Ser Trp Thr Arg Ala Met Asp Pro Ala
    210                 215                 220

Pro Ala Arg Ala Gln Pro Ala Met His Thr Val Asn Gly Tyr Val Asn
225                 230                 235                 240

Arg Ser Leu Pro Gly Leu Ile Gly Cys His Lys Lys Ser Val Tyr Trp
                245                 250                 255

His Val Ile Gly Met Gly Thr Ser Pro Glu Val His Ser Ile Phe Leu
                260                 265                 270

Glu Gly His Thr Phe Leu Val Arg His His Arg Gln Ala Ser Leu Glu
            275                 280                 285

Ile Ser Pro Leu Thr Phe Leu Thr Ala Gln Thr Phe Leu Met Asp Leu
    290                 295                 300

Gly Gln Phe Leu Leu Phe Cys His Ile Ser Ser His His His Gly Gly
305                 310                 315                 320

Met Glu Ala His Val Arg Val Glu Ser Cys Ala Glu Glu Pro Gln Leu
                325                 330                 335

Arg Arg Lys Ala Asp Glu Glu Asp Tyr Asp Asp Asn Leu Tyr Asp
                340                 345                 350
```

-continued

Ser Asp Met Asp Val Val Arg Leu Asp Gly Asp Val Ser Pro Phe
        355                 360                 365

Ile Gln Ile Arg Ser Val Ala Lys Lys His Pro Lys Thr Trp Val His
370                 375                 380

Tyr Ile Ser Ala Glu Glu Asp Trp Asp Tyr Ala Pro Ala Val Pro
385                 390                 395                 400

Ser Pro Ser Asp Arg Ser Tyr Lys Ser Leu Tyr Leu Asn Ser Gly Pro
                405                 410                 415

Gln Arg Ile Gly Arg Lys Tyr Lys Lys Ala Arg Phe Val Ala Tyr Thr
                420                 425                 430

Asp Val Thr Phe Lys Thr Arg Lys Ala Ile Pro Tyr Glu Ser Gly Ile
            435                 440                 445

Leu Gly Pro Leu Leu Tyr Gly Glu Val Gly Asp Thr Leu Leu Ile Ile
450                 455                 460

Phe Lys Asn Lys Ala Ser Arg Pro Tyr Asn Ile Tyr Pro His Gly Ile
465                 470                 475                 480

Thr Asp Val Ser Ala Leu His Pro Gly Arg Leu Leu Lys Gly Trp Lys
                485                 490                 495

His Leu Lys Asp Met Pro Ile Leu Pro Gly Glu Thr Phe Lys Tyr Lys
                500                 505                 510

Trp Thr Val Thr Val Glu Asp Gly Pro Thr Lys Ser Asp Pro Arg Cys
            515                 520                 525

Leu Thr Arg Tyr Tyr Ser Ser Ser Ile Asn Leu Glu Lys Asp Leu Ala
        530                 535                 540

Ser Gly Leu Ile Gly Pro Leu Leu Ile Cys Tyr Lys Glu Ser Val Asp
545                 550                 555                 560

Gln Arg Gly Asn Gln Met Met Ser Asp Lys Arg Asn Val Ile Leu Phe
                565                 570                 575

Ser Val Phe Asp Glu Asn Gln Ser Trp Tyr Leu Ala Glu Asn Ile Gln
                580                 585                 590

Arg Phe Leu Pro Asn Pro Asp Gly Leu Gln Pro Gln Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Val Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
            675                 680                 685

Val Leu Gly Cys His Asn Ser Asp Leu Arg Asn Arg Gly Met Thr Ala
    690                 695                 700

Leu Leu Lys Val Tyr Ser Cys Asp Arg Asp Ile Gly Asp Tyr Tyr Asp
705                 710                 715                 720

Asn Thr Tyr Glu Asp Ile Pro Gly Phe Leu Leu Ser Gly Lys Asn Val
                725                 730                 735

Ile Glu Pro Arg Ser Phe Ala Gln Asn Ser Arg Pro Pro Ser Ala Ser
                740                 745                 750

Gln Lys Gln Phe Gln Thr Ile Thr Ser Pro Glu Asp Asp Val Glu Leu
        755                 760                 765

```
Asp Pro Gln Ser Gly Glu Arg Thr Gln Ala Leu Glu Glu Leu Ser Val
770                 775                 780

Pro Ser Gly Asp Gly Ser Met Leu Leu Gly Gln Asn Pro Ala Pro His
785                 790                 795                 800

Gly Ser Ser Ser Asp Leu Gln Glu Ala Arg Asn Glu Ala Asp Asp
                805                 810                 815

Tyr Leu Pro Gly Ala Arg Glu Arg Asn Thr Ala Pro Ser Ala Ala Ala
                820                 825                 830

Arg Leu Arg Pro Glu Leu His His Ser Ala Glu Arg Val Leu Thr Pro
                835                 840                 845

Glu Pro Glu Lys Glu Leu Lys Lys Leu Asp Ser Lys Met Ser Ser Ser
850                 855                 860

Ser Asp Leu Leu Lys Thr Ser Pro Thr Ile Pro Ser Asp Thr Leu Ser
865                 870                 875                 880

Ala Glu Thr Glu Arg Thr His Ser Leu Gly Pro His Pro Gln Val
                885                 890                 895

Asn Phe Arg Ser Gln Leu Gly Ala Ile Val Leu Gly Lys Asn Ser Ser
                900                 905                 910

His Phe Ile Gly Ala Gly Val Pro Leu Gly Ser Thr Glu Glu Asp His
                915                 920                 925

Glu Ser Ser Leu Gly Glu Asn Val Ser Pro Val Glu Ser Asp Gly Ile
930                 935                 940

Phe Glu Lys Glu Arg Ala His Gly Pro Ala Ser Leu Thr Lys Asp Asp
945                 950                 955                 960

Val Leu Phe Lys Val Asn Ile Ser Leu Val Lys Thr Asn Lys Ala Arg
                965                 970                 975

Val Tyr Leu Lys Thr Asn Arg Lys Ile His Ile Asp Asp Ala Ala Leu
                980                 985                 990

Leu Thr Glu Asn Arg Ala Ser Ala  Thr Phe Met Asp Lys  Asn Thr Thr
          995                 1000                1005

Ala Ser  Gly Leu Asn His Val  Ser Asn Trp Ile Lys  Gly Pro Leu
    1010                1015                1020

Gly Lys  Asn Pro Leu Ser Ser  Glu Arg Gly Pro Ser  Pro Glu Leu
    1025                1030                1035

Leu Thr  Ser Ser Gly Ser Gly  Lys Ser Val Lys Gly  Gln Ser Ser
    1040                1045                1050

Gly Gln  Gly Arg Ile Arg Val  Ala Val Glu Glu Glu  Glu Leu Ser
    1055                1060                1065

Lys Gly  Lys Glu Met Met Leu  Pro Asn Ser Glu Leu  Thr Phe Leu
    1070                1075                1080

Thr Asn  Ser Ala Asp Val Gln  Gly Asn Asp Thr His  Ser Gln Gly
    1085                1090                1095

Lys Lys  Ser Arg Glu Glu Met  Glu Arg Arg Glu Lys  Leu Val Gln
    1100                1105                1110

Glu Lys  Val Asp Leu Pro Gln  Val Tyr Thr Ala Thr  Gly Thr Lys
    1115                1120                1125

Asn Phe  Leu Arg Asn Ile Phe  His Gln Ser Thr Glu  Pro Ser Val
    1130                1135                1140

Glu Gly  Phe Asp Gly Gly Ser  His Ala Pro Val Pro  Gln Asp Ser
    1145                1150                1155

Arg Ser  Leu Asn Asp Ser Ala  Glu Arg Ala Glu Thr  His Ile Ala
    1160                1165                1170

His Phe  Ser Ala Ile Arg Glu  Glu Ala Pro Leu Glu  Ala Pro Gly
```

```
            1175                1180                1185
Asn Arg Thr Gly Pro Gly Pro Arg Ser Ala Val Pro Arg Arg Val
        1190                1195                1200
Lys Gln Ser Leu Lys Gln Ile Arg Leu Pro Leu Glu Glu Ile Lys
        1205                1210                1215
Pro Glu Arg Gly Val Val Leu Asn Ala Thr Ser Thr Arg Trp Ser
        1220                1225                1230
Glu Ser Ser Pro Ile Leu Gln Gly Ala Lys Arg Asn Asn Leu Ser
        1235                1240                1245
Leu Pro Phe Leu Thr Leu Glu Met Ala Gly Gly Gln Gly Lys Ile
        1250                1255                1260
Ser Ala Leu Gly Lys Ser Ala Ala Gly Pro Leu Ala Ser Gly Lys
        1265                1270                1275
Leu Glu Lys Ala Val Leu Ser Ser Ala Gly Leu Ser Glu Ala Ser
        1280                1285                1290
Gly Lys Ala Glu Phe Leu Pro Lys Val Arg Val His Arg Glu Asp
        1295                1300                1305
Leu Leu Pro Gln Lys Thr Ser Asn Val Ser Cys Ala His Gly Asp
        1310                1315                1320
Leu Gly Gln Glu Ile Phe Leu Gln Lys Thr Arg Gly Pro Val Asn
        1325                1330                1335
Leu Asn Lys Val Asn Arg Pro Gly Arg Thr Pro Ser Lys Leu Leu
        1340                1345                1350
Gly Pro Pro Met Pro Lys Glu Trp Glu Ser Leu Glu Lys Ser Pro
        1355                1360                1365
Lys Ser Thr Ala Leu Arg Thr Lys Asp Ile Ile Ser Leu Pro Leu
        1370                1375                1380
Asp Arg His Glu Ser Asn His Ser Ile Ala Ala Lys Asn Glu Gly
        1385                1390                1395
Gln Ala Glu Thr Gln Arg Glu Ala Ala Trp Thr Lys Gln Gly Gly
        1400                1405                1410
Pro Gly Arg Leu Cys Ala Pro Lys Pro Pro Val Leu Arg Arg His
        1415                1420                1425
Gln Arg Asp Ile Ser Leu Pro Thr Phe Gln Pro Glu Glu Asp Lys
        1430                1435                1440
Met Asp Tyr Asp Asp Ile Phe Ser Thr Glu Thr Lys Gly Glu Asp
        1445                1450                1455
Phe Asp Ile Tyr Gly Glu Asp Glu Asn Gln Asp Pro Arg Ser Phe
        1460                1465                1470
Gln Lys Arg Thr Arg His Tyr Phe Ile Ala Ala Val Glu Gln Leu
        1475                1480                1485
Trp Asp Tyr Gly Met Ser Glu Ser Pro Arg Ala Leu Arg Asn Arg
        1490                1495                1500
Ala Gln Asn Gly Glu Val Pro Arg Phe Lys Lys Val Val Phe Arg
        1505                1510                1515
Glu Phe Ala Asp Gly Ser Phe Thr Gln Pro Ser Tyr Arg Gly Glu
        1520                1525                1530
Leu Asn Lys His Leu Gly Leu Leu Gly Pro Tyr Ile Arg Ala Glu
        1535                1540                1545
Val Glu Asp Asn Ile Met Val Thr Phe Lys Asn Gln Ala Ser Arg
        1550                1555                1560
Pro Tyr Ser Phe Tyr Ser Ser Leu Ile Ser Tyr Pro Asp Asp Gln
        1565                1570                1575
```

-continued

```
Glu Gln Gly Ala Glu Pro Arg His Asn Phe Val Gln Pro Asn Glu
    1580            1585                1590

Thr Arg Thr Tyr Phe Trp Lys Val Gln His His Met Ala Pro Thr
    1595            1600                1605

Glu Asp Glu Phe Asp Cys Lys Ala Trp Ala Tyr Phe Ser Asp Val
    1610            1615                1620

Asp Leu Glu Lys Asp Val His Ser Gly Leu Ile Gly Pro Leu Leu
    1625            1630                1635

Ile Cys Arg Ala Asn Thr Leu Asn Ala Ala His Gly Arg Gln Val
    1640            1645                1650

Thr Val Gln Glu Phe Ala Leu Phe Phe Thr Ile Phe Asp Glu Thr
    1655            1660                1665

Lys Ser Trp Tyr Phe Thr Glu Asn Val Glu Arg Asn Cys Arg Ala
    1670            1675                1680

Pro Cys His Leu Gln Met Glu Asp Pro Thr Leu Lys Glu Asn Tyr
    1685            1690                1695

Arg Phe His Ala Ile Asn Gly Tyr Val Met Asp Thr Leu Pro Gly
    1700            1705                1710

Leu Val Met Ala Gln Asn Gln Arg Ile Arg Trp Tyr Leu Leu Ser
    1715            1720                1725

Met Gly Ser Asn Glu Asn Ile His Ser Ile His Phe Ser Gly His
    1730            1735                1740

Val Phe Ser Val Arg Lys Lys Glu Glu Tyr Lys Met Ala Val Tyr
    1745            1750                1755

Asn Leu Tyr Pro Gly Val Phe Glu Thr Val Glu Met Leu Pro Ser
    1760            1765                1770

Lys Val Gly Ile Trp Arg Ile Glu Cys Leu Ile Gly Glu His Leu
    1775            1780                1785

Gln Ala Gly Met Ser Thr Thr Phe Leu Val Tyr Ser Lys Glu Cys
    1790            1795                1800

Gln Ala Pro Leu Gly Met Ala Ser Gly Arg Ile Arg Asp Phe Gln
    1805            1810                1815

Ile Thr Ala Ser Gly Gln Tyr Gly Gln Trp Ala Pro Lys Leu Ala
    1820            1825                1830

Arg Leu His Tyr Ser Gly Ser Ile Asn Ala Trp Ser Thr Lys Asp
    1835            1840                1845

Pro His Ser Trp Ile Lys Val Asp Leu Leu Ala Pro Met Ile Ile
    1850            1855                1860

His Gly Ile Met Thr Gln Gly Ala Arg Gln Lys Phe Ser Ser Leu
    1865            1870                1875

Tyr Ile Ser Gln Phe Ile Ile Met Tyr Ser Leu Asp Gly Arg Asn
    1880            1885                1890

Trp Gln Ser Tyr Arg Gly Asn Ser Thr Gly Thr Leu Met Val Phe
    1895            1900                1905

Phe Gly Asn Val Asp Ala Ser Gly Ile Lys His Asn Ile Phe Asn
    1910            1915                1920

Pro Pro Ile Val Ala Arg Tyr Ile Arg Leu His Pro Thr His Tyr
    1925            1930                1935

Ser Ile Arg Ser Thr Leu Arg Met Glu Leu Met Gly Cys Asp Leu
    1940            1945                1950

Asn Ser Cys Ser Met Pro Leu Gly Met Gln Asn Lys Ala Ile Ser
    1955            1960                1965
```

```
Asp Ser Gln Ile Thr Ala Ser Ser His Leu Ser Asn Ile Phe Ala
    1970                1975                1980

Thr Trp Ser Pro Ser Gln Ala Arg Leu His Leu Gln Gly Arg Thr
    1985                1990                1995

Asn Ala Trp Arg Pro Arg Val Ser Ser Ala Glu Glu Trp Leu Gln
    2000                2005                2010

Val Asp Leu Gln Lys Thr Val Lys Val Thr Gly Ile Thr Thr Gln
    2015                2020                2025

Gly Val Lys Ser Leu Leu Ser Ser Met Tyr Val Lys Glu Phe Leu
    2030                2035                2040

Val Ser Ser Ser Gln Asp Gly Arg Arg Trp Thr Leu Phe Leu Gln
    2045                2050                2055

Asp Gly His Thr Lys Val Phe Gln Gly Asn Gln Asp Ser Ser Thr
    2060                2065                2070

Pro Val Val Asn Ala Leu Asp Pro Pro Leu Phe Thr Arg Tyr Leu
    2075                2080                2085

Arg Ile His Pro Thr Ser Trp Ala Gln His Ile Ala Leu Arg Leu
    2090                2095                2100

Glu Val Leu Gly Cys Glu Ala Gln Asp Leu Tyr
    2105            2110
```

<210> SEQ ID NO 8
<211> LENGTH: 2332
<212> TYPE: PRT
<213> ORGANISM: homo sapiens

<400> SEQUENCE: 8

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
                20                  25                  30

Arg Val Pro Lys Ser Phe Pro Phe Asn Thr Ser Val Val Tyr Lys Lys
            35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220
```

```
Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
            245                 250                 255

Val Ile Gly Met Gly Thr Thr Pro Glu Val His Ser Ile Phe Leu Glu
        260                 265                 270

Gly His Thr Phe Leu Val Arg Asn His Arg Gln Ala Ser Leu Glu Ile
    275                 280                 285

Ser Pro Ile Thr Phe Leu Thr Ala Gln Thr Leu Leu Met Asp Leu Gly
290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640
```

-continued

Ser Ile Gly Ala Gln Thr Asp Phe Leu Ser Val Phe Phe Ser Gly Tyr
            645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys
            755                 760                 765

Thr Asp Pro Trp Phe Ala His Arg Thr Pro Met Pro Lys Ile Gln Asn
    770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
            835                 840                 845

Phe Thr Pro Glu Ser Gly Leu Gln Leu Arg Leu Asn Glu Lys Leu Gly
    850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
    915                 920                 925

Leu Thr Glu Ser Gly Gly Pro Leu Ser Leu Ser Glu Glu Asn Asn Asp
    930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
            995                1000                1005

Thr Asn Arg Lys Thr His Ile Asp Gly Pro Ser Leu Leu Ile Glu
    1010                1015                1020

Asn Ser Pro Ser Val Trp Gln Asn Ile Leu Glu Ser Asp Thr Glu
    1025                1030                1035

Phe Lys Lys Val Thr Pro Leu Ile His Asp Arg Met Leu Met Asp
    1040                1045                1050

Lys Asn Ala Thr Ala Leu Arg Leu Asn His Met Ser Asn Lys Thr 1055                1060                1065

Thr Ser Ser Lys Asn Met Glu Met Val Gln Gln Lys Lys Glu Gly
        1070                1075                1080

Pro Ile Pro Pro Asp Ala Gln Asn Pro Asp Met Ser Phe Phe Lys
        1085                1090                1095

Met Leu Phe Leu Pro Glu Ser Ala Arg Trp Ile Gln Arg Thr His
        1100                1105                1110

Gly Lys Asn Ser Leu Asn Ser Gly Gln Gly Pro Ser Pro Lys Gln
        1115                1120                1125

Leu Val Ser Leu Gly Pro Glu Lys Ser Val Glu Gly Gln Asn Phe
        1130                1135                1140

Leu Ser Glu Lys Asn Lys Val Val Gly Lys Gly Glu Phe Thr
        1145                1150                1155

Lys Asp Val Gly Leu Lys Glu Met Val Phe Pro Ser Ser Arg Asn
        1160                1165                1170

Leu Phe Leu Thr Asn Leu Asp Asn Leu His Glu Asn Asn Thr His
        1175                1180                1185

Asn Gln Glu Lys Lys Ile Gln Glu Ile Glu Lys Lys Glu Thr
        1190                1195                1200

Leu Ile Gln Glu Asn Val Val Leu Pro Gln Ile His Thr Val Thr
        1205                1210                1215

Gly Thr Lys Asn Phe Met Lys Asn Leu Phe Leu Leu Ser Thr Arg
        1220                1225                1230

Gln Asn Val Glu Gly Ser Tyr Asp Gly Ala Tyr Ala Pro Val Leu
        1235                1240                1245

Gln Asp Phe Arg Ser Leu Asn Asp Ser Thr Asn Arg Thr Lys Lys
        1250                1255                1260

His Thr Ala His Phe Ser Lys Lys Gly Glu Glu Glu Asn Leu Glu
        1265                1270                1275

Gly Leu Gly Asn Gln Thr Lys Gln Ile Val Glu Lys Tyr Ala Cys
        1280                1285                1290

Thr Thr Arg Ile Ser Pro Asn Thr Ser Gln Gln Asn Phe Val Thr
        1295                1300                1305

Gln Arg Ser Lys Arg Ala Leu Lys Gln Phe Arg Leu Pro Leu Glu
        1310                1315                1320

Glu Thr Glu Leu Glu Lys Arg Ile Ile Val Asp Asp Thr Ser Thr
        1325                1330                1335

Gln Trp Ser Lys Asn Met Lys His Leu Thr Pro Ser Thr Leu Thr
        1340                1345                1350

Gln Ile Asp Tyr Asn Glu Lys Glu Lys Gly Ala Ile Thr Gln Ser
        1355                1360                1365

Pro Leu Ser Asp Cys Leu Thr Arg Ser His Ser Ile Pro Gln Ala
        1370                1375                1380

Asn Arg Ser Pro Leu Pro Ile Ala Lys Val Ser Ser Phe Pro Ser
        1385                1390                1395

Ile Arg Pro Ile Tyr Leu Thr Arg Val Leu Phe Gln Asp Asn Ser
        1400                1405                1410

Ser His Leu Pro Ala Ala Ser Tyr Arg Lys Lys Asp Ser Gly Val
        1415                1420                1425

Gln Glu Ser Ser His Phe Leu Gln Gly Ala Lys Lys Asn Asn Leu
        1430                1435                1440

Ser Leu Ala Ile Leu Thr Leu Glu Met Thr Gly Asp Gln Arg Glu
        1445                1450                1455

Val Gly Ser Leu Gly Thr Ser Ala Thr Asn Ser Val Thr Tyr Lys
1460                1465                1470

Lys Val Glu Asn Thr Val Leu Pro Lys Pro Asp Leu Pro Lys Thr
1475                1480                1485

Ser Gly Lys Val Glu Leu Leu Pro Lys Val His Ile Tyr Gln Lys
1490                1495                1500

Asp Leu Phe Pro Thr Glu Thr Ser Asn Gly Ser Pro Gly His Leu
1505                1510                1515

Asp Leu Val Glu Gly Ser Leu Leu Gln Gly Thr Glu Gly Ala Ile
1520                1525                1530

Lys Trp Asn Glu Ala Asn Arg Pro Gly Lys Val Pro Phe Leu Arg
1535                1540                1545

Val Ala Thr Glu Ser Ser Ala Lys Thr Pro Ser Lys Leu Leu Asp
1550                1555                1560

Pro Leu Ala Trp Asp Asn His Tyr Gly Thr Gln Ile Pro Lys Glu
1565                1570                1575

Glu Trp Lys Ser Gln Glu Lys Ser Pro Glu Lys Thr Ala Phe Lys
1580                1585                1590

Lys Lys Asp Thr Ile Leu Ser Leu Asn Ala Cys Glu Ser Asn His
1595                1600                1605

Ala Ile Ala Ala Ile Asn Glu Gly Gln Asn Lys Pro Glu Ile Glu
1610                1615                1620

Val Thr Trp Ala Lys Gln Gly Arg Thr Glu Arg Leu Cys Ser Gln
1625                1630                1635

Asn Pro Pro Val Leu Lys Arg His Gln Arg Glu Ile Thr Arg Thr
1640                1645                1650

Thr Leu Gln Ser Asp Gln Glu Glu Ile Asp Tyr Asp Asp Thr Ile
1655                1660                1665

Ser Val Glu Met Lys Lys Glu Asp Phe Asp Ile Tyr Asp Glu Asp
1670                1675                1680

Glu Asn Gln Ser Pro Arg Ser Phe Gln Lys Lys Thr Arg His Tyr
1685                1690                1695

Phe Ile Ala Ala Val Glu Arg Leu Trp Asp Tyr Gly Met Ser Ser
1700                1705                1710

Ser Pro His Val Leu Arg Asn Arg Ala Gln Ser Gly Ser Val Pro
1715                1720                1725

Gln Phe Lys Lys Val Val Phe Gln Glu Phe Thr Asp Gly Ser Phe
1730                1735                1740

Thr Gln Pro Leu Tyr Arg Gly Glu Leu Asn Glu His Leu Gly Leu
1745                1750                1755

Leu Gly Pro Tyr Ile Arg Ala Glu Val Glu Asp Asn Ile Met Val
1760                1765                1770

Thr Phe Arg Asn Gln Ala Ser Arg Pro Tyr Ser Phe Tyr Ser Ser
1775                1780                1785

Leu Ile Ser Tyr Glu Glu Asp Gln Arg Gln Gly Ala Glu Pro Arg
1790                1795                1800

Lys Asn Phe Val Lys Pro Asn Glu Thr Lys Thr Tyr Phe Trp Lys
1805                1810                1815

Val Gln His His Met Ala Pro Thr Lys Asp Glu Phe Asp Cys Lys
1820                1825                1830

Ala Trp Ala Tyr Phe Ser Asp Val Asp Leu Glu Lys Asp Val His
1835                1840                1845

```
Ser Gly Leu Ile Gly Pro Leu Leu Val Cys His Thr Asn Thr Leu
    1850             1855                 1860

Asn Pro Ala His Gly Arg Gln Val Thr Val Gln Glu Phe Ala Leu
    1865             1870                 1875

Phe Phe Thr Ile Phe Asp Glu Thr Lys Ser Trp Tyr Phe Thr Glu
    1880             1885                 1890

Asn Met Glu Arg Asn Cys Arg Ala Pro Cys Asn Ile Gln Met Glu
    1895             1900                 1905

Asp Pro Thr Phe Lys Glu Asn Tyr Arg Phe His Ala Ile Asn Gly
    1910             1915                 1920

Tyr Ile Met Asp Thr Leu Pro Gly Leu Val Met Ala Gln Asp Gln
    1925             1930                 1935

Arg Ile Arg Trp Tyr Leu Leu Ser Met Gly Ser Asn Glu Asn Ile
    1940             1945                 1950

His Ser Ile His Phe Ser Gly His Val Phe Thr Val Arg Lys Lys
    1955             1960                 1965

Glu Glu Tyr Lys Met Ala Leu Tyr Asn Leu Tyr Pro Gly Val Phe
    1970             1975                 1980

Glu Thr Val Glu Met Leu Pro Ser Lys Ala Gly Ile Trp Arg Val
    1985             1990                 1995

Glu Cys Leu Ile Gly Glu His Leu His Ala Gly Met Ser Thr Leu
    2000             2005                 2010

Phe Leu Val Tyr Ser Asn Lys Cys Gln Thr Pro Leu Gly Met Ala
    2015             2020                 2025

Ser Gly His Ile Arg Asp Phe Gln Ile Thr Ala Ser Gly Gln Tyr
    2030             2035                 2040

Gly Gln Trp Ala Pro Lys Leu Ala Arg Leu His Tyr Ser Gly Ser
    2045             2050                 2055

Ile Asn Ala Trp Ser Thr Lys Glu Pro Phe Ser Trp Ile Lys Val
    2060             2065                 2070

Asp Leu Leu Ala Pro Met Ile Ile His Gly Ile Lys Thr Gln Gly
    2075             2080                 2085

Ala Arg Gln Lys Phe Ser Ser Leu Tyr Ile Ser Gln Phe Ile Ile
    2090             2095                 2100

Met Tyr Ser Leu Asp Gly Lys Lys Trp Gln Thr Tyr Arg Gly Asn
    2105             2110                 2115

Ser Thr Gly Thr Leu Met Val Phe Phe Gly Asn Val Asp Ser Ser
    2120             2125                 2130

Gly Ile Lys His Asn Ile Phe Asn Pro Pro Ile Ile Ala Arg Tyr
    2135             2140                 2145

Ile Arg Leu His Pro Thr His Tyr Ser Ile Arg Ser Thr Leu Arg
    2150             2155                 2160

Met Glu Leu Met Gly Cys Asp Leu Asn Ser Cys Ser Met Pro Leu
    2165             2170                 2175

Gly Met Glu Ser Lys Ala Ile Ser Asp Ala Gln Ile Thr Ala Ser
    2180             2185                 2190

Ser Tyr Phe Thr Asn Met Phe Ala Thr Trp Ser Pro Ser Lys Ala
    2195             2200                 2205

Arg Leu His Leu Gln Gly Arg Ser Asn Ala Trp Arg Pro Gln Val
    2210             2215                 2220

Asn Asn Pro Lys Glu Trp Leu Gln Val Asp Phe Gln Lys Thr Met
    2225             2230                 2235

Lys Val Thr Gly Val Thr Thr Gln Gly Val Lys Ser Leu Leu Thr
```

-continued

```
                    2240                2245                2250
Ser Met Tyr Val Lys Glu Phe Leu Ile Ser Ser Gln Asp Gly
        2255                2260                2265

His Gln Trp Thr Leu Phe Phe Gln Asn Gly Lys Val Lys Val Phe
        2270                2275                2280

Gln Gly Asn Gln Asp Ser Phe Thr Pro Val Val Asn Ser Leu Asp
        2285                2290                2295

Pro Pro Leu Leu Thr Arg Tyr Leu Arg Ile His Pro Gln Ser Trp
        2300                2305                2310

Val His Gln Ile Ala Leu Arg Met Glu Val Leu Gly Cys Glu Ala
        2315                2320                2325

Gln Asp Leu Tyr
        2330

<210> SEQ ID NO 9
<211> LENGTH: 2324
<212> TYPE: PRT
<213> ORGANISM: canis familiaris

<400> SEQUENCE: 9

Ala Thr Arg Lys Tyr Tyr Leu Gly Ala Val Glu Leu Ser Trp Asp Tyr
  1               5                  10                  15

Met Gln Ser Asp Leu Leu Ser Ala Leu His Ala Asp Thr Ser Phe Ser
                20                  25                  30

Ser Arg Val Pro Gly Ser Leu Pro Leu Thr Thr Ser Val Thr Tyr Arg
            35                  40                  45

Lys Thr Val Phe Val Glu Phe Thr Asp Asp Leu Phe Asn Ile Ala Lys
        50                  55                  60

Pro Arg Pro Pro Trp Met Gly Leu Leu Gly Pro Thr Ile Gln Ala Glu
    65                  70                  75                  80

Val Tyr Asp Thr Val Val Ile Val Leu Lys Asn Met Ala Ser His Pro
                85                  90                  95

Val Ser Leu His Ala Val Gly Val Ser Tyr Trp Lys Ala Ser Glu Gly
            100                 105                 110

Ala Glu Tyr Glu Asp Gln Thr Ser Gln Lys Glu Lys Glu Asp Asp Asn
        115                 120                 125

Val Ile Pro Gly Glu Ser His Thr Tyr Val Trp Gln Val Leu Lys Glu
    130                 135                 140

Asn Gly Pro Met Ala Ser Asp Pro Pro Cys Leu Thr Tyr Ser Tyr Phe
145                 150                 155                 160

Ser His Val Asp Leu Val Lys Asp Leu Asn Ser Gly Leu Ile Gly Ala
                165                 170                 175

Leu Leu Val Cys Lys Glu Gly Ser Leu Ala Lys Glu Arg Thr Gln Thr
            180                 185                 190

Leu Gln Glu Phe Val Leu Leu Phe Ala Val Phe Asp Glu Gly Lys Ser
        195                 200                 205

Trp His Ser Glu Thr Asn Ala Ser Leu Thr Gln Ala Glu Ala Gln His
    210                 215                 220

Glu Leu His Thr Ile Asn Gly Tyr Val Asn Arg Ser Leu Pro Gly Leu
225                 230                 235                 240

Thr Val Cys His Lys Arg Ser Val Tyr Trp His Val Ile Gly Met Gly
                245                 250                 255

Thr Thr Pro Glu Val His Ser Ile Phe Leu Glu Gly His Thr Phe Leu
            260                 265                 270
```

```
Val Arg Asn His Arg Gln Ala Ser Leu Glu Ile Ser Pro Ile Thr Phe
        275                 280                 285

Leu Thr Ala Gln Thr Phe Leu Met Asp Leu Gly Gln Phe Leu Leu Phe
    290                 295                 300

Cys His Ile Pro Ser His Gln His Asp Gly Met Glu Ala Tyr Val Lys
305                 310                 315                 320

Val Asp Ser Cys Pro Glu Glu Pro Gln Leu Arg Met Lys Asn Asn Glu
                325                 330                 335

Asp Lys Asp Tyr Asp Asp Gly Leu Tyr Asp Ser Asp Met Asp Val Val
            340                 345                 350

Ser Phe Asp Asp Asp Ser Ser Ser Pro Phe Ile Gln Ile Arg Ser Val
        355                 360                 365

Ala Lys Lys His Pro Lys Thr Trp Val His Tyr Ile Ala Ala Glu Glu
    370                 375                 380

Glu Asp Trp Asp Tyr Ala Pro Ser Gly Pro Thr Pro Asn Asp Arg Ser
385                 390                 395                 400

His Lys Asn Leu Tyr Leu Asn Asn Gly Pro Gln Arg Ile Gly Lys Lys
                405                 410                 415

Tyr Lys Lys Val Arg Phe Val Ala Tyr Thr Asp Glu Thr Phe Lys Thr
            420                 425                 430

Arg Glu Ala Ile Gln Tyr Glu Ser Gly Ile Leu Gly Pro Leu Leu Tyr
        435                 440                 445

Gly Glu Val Gly Asp Thr Leu Leu Ile Ile Phe Lys Asn Gln Ala Ser
    450                 455                 460

Arg Pro Tyr Asn Ile Tyr Pro His Gly Ile Asn Tyr Val Thr Pro Leu
465                 470                 475                 480

His Thr Gly Arg Leu Pro Lys Gly Val Lys His Leu Lys Asp Met Pro
                485                 490                 495

Ile Leu Pro Gly Glu Ile Phe Lys Tyr Lys Trp Thr Val Thr Val Glu
            500                 505                 510

Asp Gly Pro Thr Lys Ser Asp Pro Arg Cys Leu Thr Arg Tyr Tyr Ser
        515                 520                 525

Ser Phe Ile Asn Leu Glu Arg Asp Leu Ala Ser Gly Leu Ile Gly Pro
    530                 535                 540

Leu Leu Ile Cys Tyr Lys Glu Ser Val Asp Gln Arg Gly Asn Gln Met
545                 550                 555                 560

Met Ser Asp Lys Arg Asn Val Ile Leu Phe Ser Val Phe Asp Glu Asn
                565                 570                 575

Arg Ser Trp Tyr Leu Thr Glu Asn Met Gln Arg Phe Leu Pro Asn Ala
            580                 585                 590

Asp Val Val Gln Pro His Asp Pro Glu Phe Gln Leu Ser Asn Ile Met
        595                 600                 605

His Ser Ile Asn Gly Tyr Val Phe Asp Asn Leu Gln Leu Ser Val Cys
    610                 615                 620

Leu His Glu Val Ala Tyr Trp Tyr Ile Leu Ser Val Gly Ala Gln Thr
625                 630                 635                 640

Asp Phe Leu Ser Val Phe Phe Ser Gly Tyr Thr Phe Lys His Lys Met
                645                 650                 655

Val Tyr Glu Asp Thr Leu Thr Leu Phe Pro Phe Ser Gly Glu Thr Val
            660                 665                 670

Phe Met Ser Met Glu Asn Pro Gly Leu Trp Val Leu Gly Cys His Asn
        675                 680                 685

Ser Asp Phe Arg Asn Arg Gly Met Thr Ala Leu Leu Lys Val Ser Ser
```

```
                690             695             700
Cys Asn Arg Asn Ile Asp Asp Tyr Tyr Glu Asp Thr Tyr Glu Asp Ile
705             710             715             720

Pro Thr Pro Leu Leu Asn Glu Asn Asn Val Ile Lys Pro Arg Ser Phe
                725             730             735

Ser Gln Asn Ser Arg His Pro Ser Thr Lys Glu Lys Gln Leu Lys Ala
            740             745             750

Thr Thr Thr Pro Glu Asn Asp Ile Glu Lys Ile Asp Leu Gln Ser Gly
            755             760             765

Glu Arg Thr Gln Leu Ile Lys Ala Gln Ser Val Ser Ser Ser Asp Leu
770             775             780

Leu Met Leu Leu Gly Gln Asn Pro Thr Pro Arg Gly Leu Phe Leu Ser
785             790             795             800

Asp Leu Arg Glu Ala Thr Asp Arg Ala Asp Asp His Ser Arg Gly Ala
                805             810             815

Ile Glu Arg Asn Lys Gly Pro Pro Glu Val Ala Ser Leu Arg Pro Glu
            820             825             830

Leu Arg His Ser Glu Asp Arg Glu Phe Thr Pro Glu Pro Glu Leu Gln
            835             840             845

Leu Arg Leu Asn Glu Asn Leu Gly Thr Asn Thr Thr Val Glu Leu Lys
850             855             860

Lys Leu Asp Leu Lys Ile Ser Ser Ser Asp Ser Leu Met Thr Ser
865             870             875             880

Pro Thr Ile Pro Ser Asp Lys Leu Ala Ala Ala Thr Glu Lys Thr Gly
                885             890             895

Ser Leu Gly Pro Pro Asn Met Ser Val His Phe Asn Ser His Leu Gly
            900             905             910

Thr Ile Val Phe Gly Asn Ser Ser His Leu Ile Gln Ser Gly Val
            915             920             925

Pro Leu Glu Leu Ser Glu Glu Asp Asn Asp Ser Lys Leu Leu Glu Ala
930             935             940

Pro Leu Met Asn Ile Gln Glu Ser Ser Leu Arg Glu Asn Val Leu Ser
945             950             955             960

Met Glu Ser Asn Arg Leu Phe Lys Glu Glu Arg Ile Arg Gly Pro Ala
                965             970             975

Ser Leu Ile Lys Asp Asn Ala Leu Phe Lys Val Asn Ile Ser Ser Val
            980             985             990

Lys Thr Asn Arg Ala Pro Val Asn Leu Thr Thr Asn Arg Lys Thr Arg
            995             1000            1005

Val Ala Ile Pro Thr Leu Leu Ile Glu Asn Ser Thr Ser Val Trp
    1010            1015            1020

Gln Asp Ile Met Leu Glu Arg Asn Thr Glu Phe Lys Glu Val Thr
    1025            1030            1035

Ser Leu Ile His Asn Glu Thr Phe Met Asp Arg Asn Thr Thr Ala
    1040            1045            1050

Leu Gly Leu Asn His Val Ser Asn Lys Thr Thr Leu Ser Lys Asn
    1055            1060            1065

Val Glu Met Ala His Gln Lys Lys Glu Asp Pro Val Pro Leu Arg
    1070            1075            1080

Ala Glu Asn Pro Asp Leu Ser Ser Ser Lys Ile Pro Phe Leu Pro
    1085            1090            1095

Asp Trp Ile Lys Thr His Gly Lys Asn Ser Leu Ser Ser Glu Gln
    1100            1105            1110
```

```
Arg Pro Ser Pro Lys Gln Leu Thr Ser Leu Gly Ser Glu Lys Ser
1115                1120                1125

Val Lys Asp Gln Asn Phe Leu Ser Glu Glu Lys Val Val Val Gly
1130                1135                1140

Glu Asp Glu Phe Thr Lys Asp Thr Glu Leu Gln Glu Ile Phe Pro
1145                1150                1155

Asn Asn Lys Ser Ile Phe Ala Asn Leu Ala Asn Val Gln Glu
1160                1165                1170

Asn Asp Thr Tyr Asn Gln Glu Lys Lys Ser Pro Glu Glu Ile Glu
1175                1180                1185

Arg Lys Glu Lys Leu Thr Gln Glu Asn Val Ala Leu Pro Gln Ala
1190                1195                1200

His Thr Met Ile Gly Thr Lys Asn Phe Leu Lys Asn Leu Phe Leu
1205                1210                1215

Leu Ser Thr Lys Gln Asn Val Ala Gly Leu Glu Glu Gln Pro Tyr
1220                1225                1230

Thr Pro Ile Leu Gln Asp Thr Arg Ser Leu Asn Asp Ser Pro His
1235                1240                1245

Ser Glu Gly Ile His Met Ala Asn Phe Ser Lys Ile Arg Glu Glu
1250                1255                1260

Ala Asn Leu Glu Gly Leu Gly Asn Gln Thr Asn Gln Met Val Glu
1265                1270                1275

Arg Phe Pro Ser Thr Thr Arg Met Ser Ser Asn Ala Ser Gln His
1280                1285                1290

Val Ile Thr Gln Arg Gly Lys Arg Ser Leu Lys Gln Pro Arg Leu
1295                1300                1305

Ser Gln Gly Glu Ile Lys Phe Glu Arg Lys Val Ile Ala Asn Asp
1310                1315                1320

Thr Ser Thr Gln Trp Ser Lys Asn Met Asn Tyr Leu Ala Gln Gly
1325                1330                1335

Thr Leu Thr Gln Ile Glu Tyr Asn Glu Lys Glu Lys Arg Ala Ile
1340                1345                1350

Thr Gln Ser Pro Leu Ser Asp Cys Ser Met Arg Asn His Val Thr
1355                1360                1365

Ile Gln Met Asn Asp Ser Ala Leu Pro Val Ala Lys Glu Ser Ala
1370                1375                1380

Ser Pro Ser Val Arg His Thr Asp Leu Thr Lys Ile Pro Ser Gln
1385                1390                1395

His Asn Ser Ser His Leu Pro Ala Ser Ala Cys Asn Tyr Thr Phe
1400                1405                1410

Arg Glu Arg Thr Ser Gly Val Gln Glu Gly Ser His Phe Leu Gln
1415                1420                1425

Glu Ala Lys Arg Asn Asn Leu Ser Leu Ala Phe Val Thr Leu Gly
1430                1435                1440

Ile Thr Glu Gly Gln Gly Lys Phe Ser Ser Leu Gly Lys Ser Ala
1445                1450                1455

Thr Asn Gln Pro Met Tyr Lys Lys Leu Glu Asn Thr Val Leu Leu
1460                1465                1470

Gln Pro Gly Leu Ser Glu Thr Ser Asp Lys Val Glu Leu Leu Ser
1475                1480                1485

Gln Val His Val Asp Gln Glu Asp Ser Phe Pro Thr Lys Thr Ser
1490                1495                1500
```

-continued

```
Asn Asp Ser Pro Gly His Leu Asp Leu Met Gly Lys Ile Phe Leu
1505                1510                1515

Gln Lys Thr Gln Gly Pro Val Lys Met Asn Lys Thr Asn Ser Pro
1520                1525                1530

Gly Lys Val Pro Phe Leu Lys Trp Ala Thr Glu Ser Ser Glu Lys
1535                1540                1545

Ile Pro Ser Lys Leu Leu Gly Val Leu Ala Trp Asp Asn His Tyr
1550                1555                1560

Asp Thr Gln Ile Pro Ser Glu Glu Trp Lys Ser Gln Lys Lys Ser
1565                1570                1575

Gln Thr Asn Thr Ala Phe Lys Arg Lys Asp Thr Ile Leu Pro Leu
1580                1585                1590

Gly Pro Cys Glu Asn Asn Asp Ser Thr Ala Ala Ile Asn Glu Gly
1595                1600                1605

Gln Asp Lys Pro Gln Arg Glu Ala Met Trp Ala Lys Gln Gly Glu
1610                1615                1620

Pro Gly Arg Leu Cys Ser Gln Asn Pro Pro Val Ser Lys His His
1625                1630                1635

Gln Arg Glu Ile Thr Val Thr Thr Leu Gln Pro Glu Glu Asp Lys
1640                1645                1650

Phe Glu Tyr Asp Asp Thr Phe Ser Ile Glu Met Lys Arg Glu Asp
1655                1660                1665

Phe Asp Ile Tyr Gly Asp Tyr Glu Asn Gln Gly Leu Arg Ser Phe
1670                1675                1680

Gln Lys Lys Thr Arg His Tyr Phe Ile Ala Ala Val Glu Arg Leu
1685                1690                1695

Trp Asp Tyr Gly Met Ser Arg Ser Pro His Ile Leu Arg Asn Arg
1700                1705                1710

Ala Gln Ser Gly Asp Val Gln Gln Phe Lys Lys Val Val Phe Gln
1715                1720                1725

Glu Phe Thr Asp Gly Ser Phe Thr Gln Pro Leu Tyr Arg Gly Glu
1730                1735                1740

Leu Asn Glu His Leu Gly Leu Leu Gly Pro Tyr Ile Arg Ala Glu
1745                1750                1755

Val Glu Asp Asn Ile Val Val Thr Phe Lys Asn Gln Ala Ser Arg
1760                1765                1770

Pro Tyr Ser Phe Tyr Ser Ser Leu Ile Ser Tyr Asp Glu Asp Glu
1775                1780                1785

Gly Gln Gly Ala Glu Pro Arg Arg Lys Phe Val Asn Pro Asn Glu
1790                1795                1800

Thr Lys Ile Tyr Phe Trp Lys Val Gln His His Met Ala Pro Thr
1805                1810                1815

Lys Asp Glu Phe Asp Cys Lys Ala Trp Ala Tyr Phe Ser Asp Val
1820                1825                1830

Asp Leu Glu Lys Asp Val His Ser Gly Leu Ile Gly Pro Leu Leu
1835                1840                1845

Ile Cys Arg Ser Asn Thr Leu Asn Pro Ala His Gly Arg Gln Val
1850                1855                1860

Thr Val Gln Glu Phe Ala Leu Val Phe Thr Ile Phe Asp Glu Thr
1865                1870                1875

Lys Ser Trp Tyr Phe Thr Glu Asn Leu Glu Arg Asn Cys Arg Ala
1880                1885                1890

Pro Cys Asn Val Gln Lys Glu Asp Pro Thr Leu Lys Glu Asn Phe
```

-continued

```
            1895                1900                1905
Arg Phe His Ala Ile Asn Gly Tyr Val Lys Asp Thr Leu Pro Gly
    1910                1915                1920
Leu Val Met Ala Gln Asp Gln Lys Val Arg Trp Tyr Leu Leu Ser
    1925                1930                1935
Met Gly Ser Asn Glu Asn Ile His Ser Ile His Phe Ser Gly His
    1940                1945                1950
Val Phe Thr Val Arg Lys Lys Glu Glu Tyr Lys Met Ala Val Tyr
    1955                1960                1965
Asn Leu Tyr Pro Gly Val Phe Glu Thr Val Glu Met Leu Pro Ser
    1970                1975                1980
Gln Val Gly Ile Trp Arg Ile Glu Cys Leu Ile Gly Glu His Leu
    1985                1990                1995
Gln Ala Gly Met Ser Thr Leu Phe Leu Val Tyr Ser Lys Lys Cys
    2000                2005                2010
Gln Thr Pro Leu Gly Met Ala Ser Gly His Ile Arg Asp Phe Gln
    2015                2020                2025
Ile Thr Ala Ser Gly Gln Tyr Gly Gln Trp Ala Pro Lys Leu Ala
    2030                2035                2040
Arg Leu His Tyr Ser Gly Ser Ile Asn Ala Trp Ser Thr Lys Asp
    2045                2050                2055
Pro Phe Ser Trp Ile Lys Val Asp Leu Leu Ala Pro Met Ile Ile
    2060                2065                2070
His Gly Ile Met Thr Gln Gly Ala Arg Gln Lys Phe Ser Ser Leu
    2075                2080                2085
Tyr Val Ser Gln Phe Ile Ile Met Tyr Ser Leu Asp Gly Asn Lys
    2090                2095                2100
Trp His Ser Tyr Arg Gly Asn Ser Thr Gly Thr Leu Met Val Phe
    2105                2110                2115
Phe Gly Asn Val Asp Ser Ser Gly Ile Lys His Asn Ile Phe Asn
    2120                2125                2130
Pro Pro Ile Ile Ala Gln Tyr Ile Arg Leu His Pro Thr His Tyr
    2135                2140                2145
Ser Ile Arg Ser Thr Leu Arg Met Glu Leu Leu Gly Cys Asp Phe
    2150                2155                2160
Asn Ser Cys Ser Met Pro Leu Gly Met Glu Ser Lys Ala Ile Ser
    2165                2170                2175
Asp Ala Gln Ile Thr Ala Ser Ser Tyr Leu Ser Ser Met Leu Ala
    2180                2185                2190
Thr Trp Ser Pro Ser Gln Ala Arg Leu His Leu Gln Gly Arg Thr
    2195                2200                2205
Asn Ala Trp Arg Pro Gln Ala Asn Asn Pro Lys Glu Trp Leu Gln
    2210                2215                2220
Val Asp Phe Arg Lys Thr Met Lys Val Thr Gly Ile Thr Thr Gln
    2225                2230                2235
Gly Val Lys Ser Leu Leu Ile Ser Met Tyr Val Lys Glu Phe Leu
    2240                2245                2250
Ile Ser Ser Ser Gln Asp Gly His Asn Trp Thr Leu Phe Leu Gln
    2255                2260                2265
Asn Gly Lys Val Lys Val Phe Gln Gly Asn Arg Asp Ser Ser Thr
    2270                2275                2280
Pro Val Arg Asn Arg Leu Glu Pro Pro Leu Val Ala Arg Tyr Val
    2285                2290                2295
```

```
Arg Leu His Pro Gln Ser Trp Ala His His Ile Ala Leu Arg Leu
    2300            2305                2310
Glu Val Leu Gly Cys Asp Thr Gln Gln Pro Ala
    2315            2320

<210> SEQ ID NO 10
<211> LENGTH: 27
<212> TYPE: PRT
<213> ORGANISM: Sus scrofa

<400> SEQUENCE: 10

Asp Ile Gly Asp Tyr Tyr Asp Asn Thr Tyr Glu Asp Ile Pro Gly Phe
1               5                   10                  15
Leu Leu Ser Gly Lys Asn Val Ile Glu Pro Arg
            20                  25

<210> SEQ ID NO 11
<211> LENGTH: 27
<212> TYPE: PRT
<213> ORGANISM: Homo sapiens

<400> SEQUENCE: 11

Asn Thr Gly Asp Tyr Tyr Glu Asp Ser Tyr Glu Asp Ile Ser Ala Tyr
1               5                   10                  15
Leu Leu Ser Lys Asn Asn Ala Ile Glu Pro Arg
            20                  25

<210> SEQ ID NO 12
<211> LENGTH: 27
<212> TYPE: PRT
<213> ORGANISM: Canis familiaris

<400> SEQUENCE: 12

Asn Ile Asp Asp Tyr Tyr Glu Asp Thr Tyr Glu Asp Ile Pro Thr Pro
1               5                   10                  15
Leu Leu Asn Glu Asn Asn Val Ile Lys Pro Arg
            20                  25
```

VARIANT OF ANTIHEMOPHILIC FACTOR VIII HAVING INCREASED SPECIFIC ACTIVITY

CROSS-REFERENCE TO RELATED APPLICATIONS AND INCORPORATION BY REFERENCE

This application is the U.S national phase pursuant to 35 U.S.C. §371 of International Application No. PCT/US2011/059297, filed Nov. 4, 2011, which claims priority to U.S. Provisional Patent Application No. 61/410,437, filed Nov. 5, 2010, the disclosures of which are incorporated herein in their entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: ASCII (text) file named "47643_SeqListing.txt"; 97,951 bytes, created May 2, 2013.

FIELD OF THE INVENTION

The present invention is in the field of blood coagulation factors and hemophilia. It relates to a new variant of antihemophilic factor VIII (FVIII), designated herein rFVIIIv3, having an increased specific activity in comparison to known factor VIII products.

BACKGROUND OF THE INVENTION

Blood clotting begins when platelets adhere to the cut wall of an injured blood vessel at a lesion site. Subsequently, in a cascade of enzymatically regulated reactions, soluble fibrinogen molecules are converted by the enzyme thrombin to insoluble strands of fibrin that hold the platelets together in a thrombus. At each step in the cascade, a variant precursor is converted to a protease that cleaves the next variant precursor in the series. Cofactors are required at most of the steps.

Factor VIII (also called antihemophilic factor VIII or FVIII) circulates as an inactive precursor in blood, bound tightly and non-covalently to von Willebrand factor. Factor VIII is proteolytically activated by thrombin or factor Xa, which dissociates it from von Willebrand factor and activates its procoagulant function in the cascade. In its active form, the variant factor VIIIa is a cofactor that increases the catalytic efficiency of factor IXa toward factor X activation by several orders of magnitude.

Cloning of human FVIII has revealed that the variant contains 2332 amino acids organized within a number of domains with the sequence A1-A2-B-A3-C1-C2 (Vehar et al., 1984, Nature 312, 337-342; Toole et al., 1984, Nature 312, 342-347 and Wood et al., 1984, Nature 312, 330-337). Most of FVIII is heterodimeric in plasma, containing a light-chain and various heavy-chain derivatives. The heterodimeric structure is due to proteolytic cleavage of the precursor at arginine$^{1648}$, resulting in heavy- and light-chains comprising $A_1$-$A_2$-B and $A_3$-$C_1$-$C_2$, respectively. The heterogeneity within the heavy chain is explained by limited proteolysis within its carboxy-terminal B-domain.

In order to function as a co-factor for factor X activation, FVIII requires limited proteolysis by factor Xa or thrombin. This activation involves cleavage at arginine at positions 372 and 740 on the heavy-chain and at position 1689 on the light-chain. It has been established that in comparison with the inactive precursor, active FVIII cofactor lacks a light chain fragment 1649-1689 and the whole B-domain (Mertens et al., 1993).

People with deficiencies in factor VIII or antibodies against factor VIII who are not treated with factor VIII suffer uncontrolled internal bleeding that may cause a range of serious symptoms, from inflammatory reactions in joints to early death. Severe hemophiliacs, who number about 10,000 in the United States, can be treated with infusion of human factor VIII, which will restore the blood's normal clotting ability if administered with sufficient frequency and concentration. The classic definition of factor VIII, in fact, is the substance present in normal blood plasma that corrects the clotting defect in plasma derived from individuals with hemophilia A.

Several preparations of human plasma-derived factor VIII of varying degrees of purity are available commercially for the treatment of hemophilia A. These include a partially purified factor VIII derived from the pooled blood of many donors that is heat- and detergent treated for viruses but contain a significant level of antigenic variants; a monoclonal antibody purified factor VIII that has lower levels of antigenic impurities and viral contamination; and recombinant human factor VIII.

The development of antibodies ("inhibitors" or "inhibitory antibodies") that inhibit the activity of factor VIII is a serious complication in the management of patients with hemophilia. Alloantibodies develop in approximately 20% of patients with hemophilia A in response to therapeutic infusions of factor VIII. In previously untreated patients with hemophilia A who develop inhibitors, the inhibitor usually develops within one year of treatment. Additionally, antibodies (autoantibodies) that inactivate factor VIII occasionally develop in individuals with previously normal factor VIII levels. If the inhibitor titer is low enough, patients can be managed by increasing the dose of factor VIII. However, often the inhibitor titer is so high that it cannot be overwhelmed by factor VIII. An alternative strategy is to bypass the need for factor VIII during normal hemostasis using activated prothrombin complex concentrate preparations (for example, KONYNE (Cutter Laboratories), FEIBA (Baxter Healthcare), PROPLEX (Baxter Healthcare)) or recombinant human factor VIIa. Additionally, since porcine factor VIII usually has substantially less reactivity with inhibitors than human factor VIII, a partially purified porcine factor VIII preparation (HYATE: C (IPSEN Pharma)) has been used. Many patients who have developed inhibitory antibodies to human factor VIII have been successfully treated with porcine factor VIII and have tolerated such treatment for long periods of time.

However, public health concerns regarding the risk of viruses or other blood-borne contaminants have limited the usefulness of porcine factor VIII purified from porcine blood. A recombinant porcine factor VIII variant has therefore been developed, which is designated "OBI-1" and described e.g. in WO 01/68109. OBI-1 is a partially B-domain deleted porcine FVIII. This molecule is presently in clinical development.

B-domain deleted factor VIII variants are known to keep the procoagulant and cofactor activity of factor VIII. In addition to this, Mertens et al. (British Journal of Haematology 1993, 85, 133-142) describe recombinant human factor VIII variants lacking the B-domain and the heavy-chain sequence spanning from Lysine 713 to Arginine 740.

Many hemophiliacs require daily replacement of factor VIII to prevent bleeding and the resulting deforming hemophilic arthropathy. In view of this, there is a need for a more potent factor VIII molecule.

SUMMARY OF THE INVENTION

In a first aspect, the invention relates to an isolated, recombinant, fully or partially B-domain deleted factor VIII (FVIII) variant, the FVIII variant being devoid of an up to 27 amino acid sequence corresponding to amino acids 716 to 742 of porcine factor VIII as depicted in FIG. 2 or amino acids 714 to 740 of SEQ ID NO: 7. This 27 amino acid sequence, NTGDYYEDSYEDISAYLLSKNNAIEPR (SEQ ID NO:10), may be partially or completely deleted.

In one embodiment, the invention relates to an isolated, recombinant, fully or partially B-domain deleted FVIII variant, the FVIII variant being devoid of an up to 27 amino acid sequence corresponding to amino acids 716 to 742 of porcine factor VIII as depicted in FIG. 2 or amino acids 714 to 740 of SEQ ID NO: 7, where 27, 26, 25, 24, 23, 22, 21, 20, 19, 18, 17, 16, 15, 14, 13, 12, 11, 10, 9, 8, 7, 6, 5, 4, 3, 2 or 1 amino acids may be deleted. In another embodiment, 27, 26, 25, 24, 23, 22, 21 or 20 amino acids are deleted. In another embodiment, 27, 26, or 25 amino acids are deleted. In another embodiment, the 27 amino acids corresponding to DIGDYYDNTYEDIPGFLLSGKNVIEPR (SEQ ID NO:10) are deleted.

In one embodiment, the invention relates to an isolated, recombinant, fully or partially B-domain deleted FVIII variant, the FVIII variant being devoid of an up to 27 amino acid sequence corresponding to amino acids 716 to 742 of human factor VIII as depicted in FIG. 2 or amino acids 714 to 740 of SEQ ID NO: 8, where 27, 26, 25, 24, 23, 22, 21, 20, 19, 18, 17, 16, 15, 14, 13, 12, 11, 10, 9, 8, 7, 6, 5, 4, 3, 2 or 1 amino acids may be deleted. In another embodiment, 27, 26, 25, 24, 23, 22, 21 or 20 amino acids are deleted. In another embodiment, 27, 26, or 25 amino acids are deleted. In another embodiment, the 27 amino acids corresponding to NTGDYYEDSYEDISAYLLSKNNAIEPR (SEQ ID NO:11) are deleted.

In another embodiment, the invention relates to an isolated, recombinant, fully or partially B-domain deleted porcine FVIII variant being completely devoid of the 27 amino acids corresponding to DIGDYYDNTYEDIPGFLLSGKNVIEPR (SEQ ID NO:10).

In another embodiment, the invention relates to an isolated, recombinant, fully or partially B-domain deleted human FVIII variant being completely devoid of the 27 amino acids corresponding to NTGDYYEDSYEDISAYLLSKNNAIEPR (SEQ ID NO:11).

In another embodiment, the invention relates to an isolated, recombinant, fully or partially B-domain deleted canine FVIII variant being completely devoid of the 27 amino acids corresponding to NIDDYYEDTYEDIPTPLLNENNVIKPR (SEQ ID NO:12).

A second aspect of the invention relates to a polynucleotide encoding a polypeptide as defined in the first aspect and the embodiments described.

In a third aspect, the invention relates to an expression vector comprising a polynucleotide as defined in the second aspect.

A fourth aspect of the invention relates to a mammalian cell comprising an expression vector as defined in the third aspect.

In a fifth aspect, the invention relates to a method for producing a FVIII as defined in the first aspect, comprising the steps of:
   a. Culturing a mammalian cell according to the fourth aspect; and
   b. Isolating from the mammalian cell the FVIII variant.

A sixth aspect of the invention relates to a pharmaceutical composition comprising a FVIII variant as defined in the first aspect.

In a seventh aspect, the invention relates to a method of treating a patient suffering from hemophilia comprising administering a therapeutically effective amount of FVIII variant according to the first aspect of the invention to a patient in need thereof, thereby treating the hemophilia in said patient.

In an eighth aspect, the invention relates to a FVIII variant according to the first aspect for use in treating hemophilia.

BRIEF DESCRIPTION OF THE DRAWINGS

FIG. 2 *a-e* are continuations of the same sequence. FIG. 2*a-e* shows a sequence alignment between the factor VIII sequences from human (*homo sapiens*), pig (*sus scrofa*), mouse (*mus musculus*) and dog (*canis familiaris*). This sequence alignment is taken from HADB (aka HAMSTeRS) 2010, home page of the Haemophilia A Mutation Database and a resource site for work on factor VIII (hadb.org.uk). The numbering follows the human sequence and is not identical to the amino acid numbers of the sequences in the Sequence Listing. The bold plus double underlined sequence depicts the sequence missing in the recombinant FVIIIv3 variants of the invention. The underlined sequence is the sequence of the B-domain. The sequence highlighted in grey is the portion from the B-domain which can be retained in the partially B-domain deleted FIIIv3 sequences of the invention.

BRIEF DESCRIPTION OF THE SEQUENCES

Figure 1:
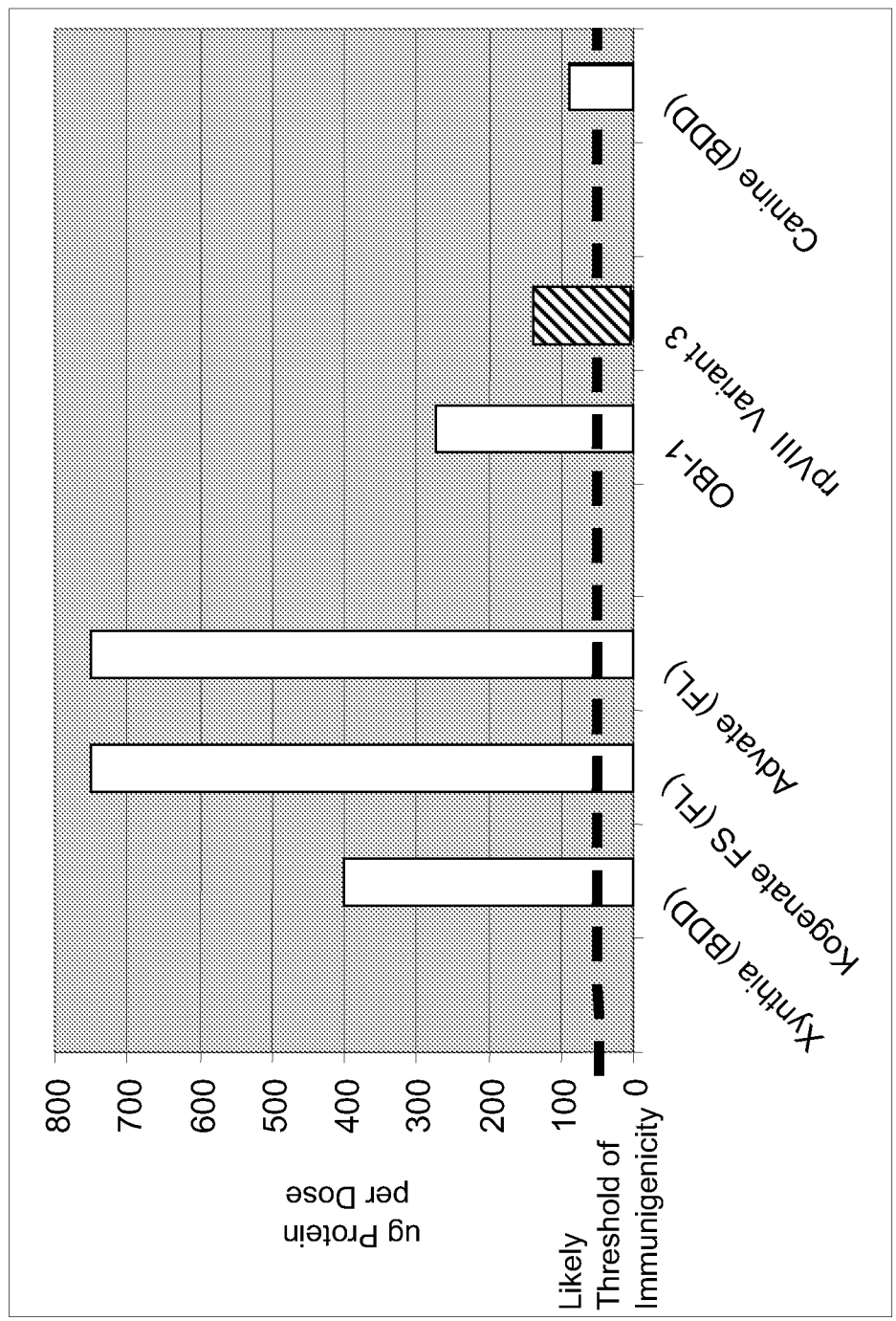
FIG. 1 shows the amount of protein in µg per dose required for 5 known FVIII products (blank columns) and the new rpFVIIIv3 (hashed column). BDD=B-domain deleted; FL=full length; u=µ.

SEQ ID NO: 1 shows the sequence of porcine partially B-domain deleted FVIIIv3;
SEQ ID NO: 2 shows the sequence of a human B-domain deleted FVIIIv3;
SEQ ID NO: 3 shows the sequence of a canine B-domain deleted FVIIIv3;
SEQ ID NO: 4 shows the sequence from the porcine FVIII B-domain that can be present in a partially B-domain deleted FVIII molecule of the invention (the so called "B-domain linker");
SEQ ID NO: 5 shows a B-domain linker sequence from the human FVIII B-domain that can be present in a partially B-domain deleted FVIII molecule of the invention;
SEQ ID NO: 6 shows a B-domain linker sequence from the canine FVIII B-domain that can be present in a partially B-domain deleted FVIII molecule of the invention;
SEQ ID NO: 7 shows the amino acid sequence of full-length porcine FVIII;
SEQ ID NO: 8 shows the amino acid sequence of full-length human FVIII;
SEQ ID NO: 9 shows the amino acid sequence of full-length canine FVIII;
SEQ ID NO:10 shows the 27 peptide sequence which corresponds to amino acids 716 to 742 of porcine factor VIII as depicted in FIG. 2 or amino acids 714 to 740 of SEQ ID NO: 7;
SEQ ID NO:11 shows the 27 peptide sequence which corresponds to amino acids 714 to 740 of human factor VIII as depicted in FIG. 2 or amino acids 714 to 740 of SEQ ID NO: 8; and SEQ ID NO:12 shows the 27 peptide sequence which corresponds to amino acids 714 to 740 of canine factor VIII as depicted in FIG. 2 or amino acids 708 to 734 of SEQ ID NO: 9.

DETAILED DESCRIPTION OF THE INVENTION

The invention is based on the finding of a variant of a partially B-domain deleted recombinant porcine factor VIII protein which contains a particular 27 amino acid deletion. This variant, which is herein designated rpFVIIIv3, has been shown to have an increased specific activity as compared to a similar protein containing the 27 amino acid stretch, namely a partially B-domain deleted recombinant porcine FVIII called "OBI-1". OBI-1, its amino acid sequence and polynucleotides encoding OBI-1 are known e.g. from U.S. Pat. No. 6,458,563.

The invention relates to an isolated, recombinant, fully or partially B-domain deleted factor VIII (FVIII) variant, wherein the FVIII variant is devoid of an amino acid sequence corresponding to amino acids 716 to 742 of porcine factor VIII as depicted in FIG. 2 or amino acids 714 to 740 of SEQ ID NO: 7.

Additionally, the invention relates to an isolated, recombinant, fully or partially B-domain deleted FVIII variant, the FVIII variant being devoid of a 27 amino acid sequence corresponding to amino acids 716 to 742 of porcine factor VIII as depicted in FIG. 2 or amino acids 714 to 740 of SEQ ID NO: 7, where 27, 26, 25, 24, 23, 22, 21, 20, 19, 18, 17, 16, 15, 14, 13, 12, 11, 10, 9, 8, 7, 6, 5, 4, 3, 2 or 1 amino acids may be deleted. In one variant, 27, 26, 25, 24, 23, 22, 21 or 20 amino acids are deleted. In another variant, 27, 26, or 25 amino acids are deleted. In the rpFVIIIv3 variant, the 27 amino acids corresponding to DIGDYYDNTYEDIPGFLLSGKNVIEPR (SEQ ID NO:10) are deleted.

Additionally, the invention relates to an isolated, recombinant, fully or partially B-domain deleted FVIII variant, the FVIII variant being devoid of a 27 amino acid sequence corresponding to amino acids 714 to 740 of human factor VIII as depicted in FIG. 2 or amino acids 714 to 740 of SEQ ID NO: 8, where 27, 26, 25, 24, 23, 22, 21, 20, 19, 18, 17, 16, 15, 14, 13, 12, 11, 10, 9, 8, 7, 6, 5, 4, 3, 2 or 1 amino acids may be deleted. In one variant, 27, 26, 25, 24, 23, 22, 21 or 20 amino acids are deleted. In another variant, 27, 26, or 25 amino acids are deleted. In a human FVIIIv3 variant (rhFVIIIv3), the 27 amino acids corresponding to NTGDYYEDSYEDISAYLLSKNNAIEPR (SEQ ID NO:11) are deleted.

Additionally, the invention relates to an isolated, recombinant, fully or partially B-domain deleted FVIII variant, the FVIII variant being devoid of a 27 amino acid sequence corresponding to amino acids 714 to 740 of canine factor VIII as depicted in FIG. 2 or amino acids 708 to 734 of SEQ ID NO: 9, where 27, 26, 25, 24, 23, 22, 21, 20, 19, 18, 17, 16, 15, 14, 13, 12, 11, 10, 9, 8, 7, 6, 5, 4, 3, 2 or 1 amino acids may be deleted. In one variant, 27, 26, 25, 24, 23, 22, 21 or 20 amino acids are deleted. In another variant, 27, 26, or 25 amino acids are deleted. In a canine FVIIIv3 variant (rcFVIIIv3), the 27 amino acids corresponding to NIDDYYEDTYEDIPTPLLNENNVIKPR (SEQ ID NO:12) are deleted.

Such variants have an elevated specific activity as compared to similar variants containing the intact 27 amino acid sequence. Preferably, the specific activity is increased by more than 25% or 30% or 35% or 40% or 45% or 50% or 55% or 60%.

The term "specific activity," as used herein, refers to the activity that will correct the coagulation defect of human factor VIII deficient plasma. Specific activity is measured in units of clotting activity per milligram total factor VIII variant in a standard assay in which the clotting time of human factor VIII deficient plasma is compared to that of normal human plasma. A suitable standard assay for measuring the potency of FVIII products, which is accepted by the FDA for high purity FVIII concentrates, is called the one-stage clotting assay (OSCA; see Example 5; Langdell R D, Wagner R H, Brinkhous K M., Effect of antihemophilic factor on one-stage clotting tests: a presumptive test for hemophilia and a simple one-stage antihemophilic assay procedure, J Lab Clin Med, 1953; 41:637-47; Brand J T, Measurement of factor VIII: a potential risk factor for vascular disease, Arch Pathol Lab Med, 1993; 117:48-51; Preston F E, Kitchen S, Quality control and factor VIII assays, Haemophilia, 1998; 4:651-3; National Committee for Clinical Laboratory Standards (NCCLS USA). Determination of factor coagulant activities; Approved guideline, NCCLS Document H-48-A 1997; 17:1-36). The amount of FVIII protein present in a sample can be measured e.g. by SEC HPLC (size-exclusion high-performance liquid chromatography).

One unit of factor VIII activity is the activity present in one milliliter of normal human plasma. In the assay, the shorter the time for clot formation, the greater the activity of the factor VIII being assayed. Porcine factor VIII has coagulation activity in a human factor VIII assay.

In line with the present invention, the terms "protein" and "polypeptide" are being used interchangeably.

Being "devoid of an amino acid sequence corresponding to amino acids 716 to 742 as depicted in FIG. 2" means that amino acids 716 and 742, as well as the amino acids between these positions, are deleted, i.e. not included, in the FVIII variant of the invention. This stretch of amino acids consists thus of 27 amino acids, of which the FVIII variants of the invention are devoid.

The factor VIII variants of the invention are herein globally designated "FVIII variant(s)" or "FVIIIv3" or "rFVIIIv3". They can be of porcine, human, canine, murine or any other origin which is appropriate for human or animal therapy. FIG. 2 depicts a sequence alignment of FVIII sequences of human, porcine, murine and canine origin.

The sequence deleted in the FVIII variants of the invention is highlighted in bold and double underlined. This stretch of amino acids can be identified for the FVIII variants of other species by the person skilled in the art by aligning the FVIII sequences of further species with e.g. the porcine or human sequence and taking the amino acids that correspond to amino acids 716 to 742 as per FIG. 2 of the present patent application.

Embodiments of the invention relate to FVIII variants of porcine, human or canine origin.

In an embodiment, the FVIII variant according to the invention comprises the sequence of SEQ ID NO:1, or a variant thereof comprising a sequence being at least 90% identical to SEQ ID NO: 1. It is understood that the 10% variability concerns the sequences outside of the deleted stretch of amino acids, i.e. that the variant is completely devoid of DIGDYYDNTYEDIPGFLLSGKNVIEPR (SEQ ID NO:10), an amino acid sequence corresponding to amino acids 716 to 742 of porcine factor VIII as depicted in FIG. 2 or amino acids 714 to 740 of SEQ ID NO: 7.

In a further embodiment, the FVIII variant of the invention comprises the sequence of SEQ ID NO:2, or a variant thereof comprising a sequence being at least 90% identical to SEQ ID NO: 2. Again, the variant is understood to be completely devoid of an amino acid sequence NTGDYYEDSYEDISAYLLSKNNAIEPR (SEQ ID NO:11), corresponding to amino acids 714 to 740 of human factor VIII as depicted in FIG. 2 or amino acids 714 to 740 of SEQ ID NO: 8.

In yet a further embodiment, the FVIII variant of the invention comprises the sequence of SEQ ID NO:3, or a variant thereof comprising a sequence being at least 90% identical to SEQ ID NO: 3. Again, the variant is understood to be completely devoid of an amino acid sequence NIDDYYEDTYE-DIPTPLLNENNVIKPR (SEQ ID NO:12) corresponding to amino acids 714 to 740 of canine factor VIII as depicted in FIG. 2 or amino acids 708 to 734 of SEQ ID NO: 9.

The FVIII variants of the invention can also comprise sequences that are at least 91, 92, 93, 94, 95, 96, 97, 98, 99, 99.5, 99.6, 99.7, 99.8 or 99.9% identical to the sequences of SEQ ID NO: 7, 8 or 9.

To determine the percent identity of two polypeptides/proteins, the amino acid sequences are aligned for optimal comparison purposes (e.g., gaps can be introduced in the sequence of a first amino acid sequence for optimal alignment with a second amino acid sequence). The amino acid residues at corresponding amino acid positions are then compared. When a position in the first sequence is occupied by the same amino acid residue as the corresponding position in the second sequence, then the molecules are identical at that position. The percent identity between the two sequences is a function of the number of identical positions shared by the sequences (i.e., % identity=# of identical positions/total # of positions (e.g., (overlapping positions)×100).

The determination of percent identity between two sequences can be accomplished using a mathematical algorithm. A preferred, non-limiting example of a mathematical algorithm utilized for the comparison of two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. Such an algorithm is incorporated into the NBLAST and XBLAST programs of Altschul, et al. (1990) J. Mol. Biol. 215:403-410. BLAST nucleotide searches can be performed with the NBLAST program, score=100, wordlength=12 to obtain nucleotide sequences homologous to a nucleic acid molecules of the invention. BLAST variant searches can be performed with the XBLAST program, score=50, wordlength=3 to obtain amino acid sequences homologous to a variant molecules of the invention. To obtain gapped alignments for comparison purposes, Gapped BLAST can be utilized as described in Altschul et al. (1997) Nucleic Acids Res. 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller, (1988) CABIOS 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) Proc. Natl. Acad. Sci. USA 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The FVIII variant of the invention can be partially or fully B-domain deleted. This means that either the whole B-domain is deleted, or a part of the B-domain is retained in the FVIII variant. The remaining (retained) part of the B-domain is e.g. selected from the 20, 15, 12, 10 or 5 N-terminal amino acids and the 20, 15, 12, 10 or 5 C-terminal amino acids of the B-domain, fused in frame with each other.

Hence, preferably, in the partially B-domain deleted FVIII variants of the invention, significant portions of the approximately 900 amino acid B-domain are being removed. In embodiments of the invention, less than 5% or less than 4% or less than 3% or less than 2% or less than 1% of the B-domain remain present in the FVIII variants.

In embodiments of the invention, the remaining portion of the B-domain is selected from a sequence consisting of SEQ ID NO: 4 or SEQ ID NO:5 or SEQ ID NO: 6.

In a further aspect, the invention relates to a polynucleotide encoding a polypeptide/protein as described above. A polynucleotide can be an RNA or DNA molecule whose nucleotide sequence embodies coding information to a host cell for the amino acid sequence of the variant of the invention, according to the known relationships of the genetic code.

In a further aspect, the invention relates to an expression vector comprising a polynucleotide as described above.

An "expression vector" is a DNA element, often of circular structure, having the ability to replicate autonomously in a desired host cell, or to integrate into a host cell genome and also possessing certain well-known features which permit expression of a coding DNA inserted into the vector sequence at the proper site and in proper orientation. Such features can include, but are not limited to, one or more promoter sequences to direct transcription initiation of the coding DNA and other DNA elements such as enhancers, polyadenylation sites and the like, all as well known in the art. The term "expression vector" is used to denote both a vector having a DNA coding sequence to be expressed inserted within its sequence, and a vector having the requisite expression control elements so arranged with respect to an insertion site that it can serve to express any coding DNA inserted into the site, all as well-known in the art. Thus, for example, a vector lacking a promoter can become an expression vector by the insertion of a promoter combined with a coding DNA. An expression vector, as used herein, can also be a viral vector.

Expression of the recombinant FVIII variants of the invention is preferably carried out in mammalian cell culture.

Therefore, in a further aspect, the invention relates to a mammalian cell comprising an expression vector as described above. For instance, CHO (Chinese hamster ovary) cells and BHK cells (baby hamster kidney cells) are mammalian cells that are suitable host cells in the context of the present invention.

In accordance with another aspect of the invention, a method for producing a FVIII variant of the invention comprises the steps of:
a. Culturing a mammalian cell as described above; and
b. Isolating from the mammalian cell the FVIII variant.

In an embodiment, the method further comprises the step of
c. Formulating the factor VIII variant together with appropriate excipients into a pharmaceutical composition.

Excipients suitable for human or animal administration are e.g. pharmaceutical stabilization compounds, preservatives, delivery vehicles, and/or carrier vehicles. One suitable formulation for factor VIII products is e.g. described in WO 03/080108, which is incorporated by reference herein.

In a further aspect, the invention relates to a pharmaceutical composition comprising a FVIII variant of the invention.

A further aspect of the invention relates to a method of treating a patient suffering from factor VIII deficiency comprising administering a therapeutically effective amount of FVIII variant of the invention to a patient in need thereof, thereby treating the factor VIII deficiency in said patient.

The term "therapeutically effective amount" as used herein, means the level of FVIII in the plasma of a patient having FVIII deficiency, who has received a pharmaceutical composition of FVIII variant, that is sufficient to exhibit a measurable improvement or protective effect in the patient (e.g., to stop bleeding). The patients having FVIII deficiency are typically congenital hemophilia A patients but also include those subjects diagnosed with "acquired hemophilia", a condition in which those who are not congenital hemophiliacs spontaneously develop inhibitory antibodies to their FVIII, creating a serious FVIII deficiency.

The invention also relates to a FVIII variant of the invention for use in treating factor VIII deficiency.

Treatment can take the form of a single intravenous administration of the composition or periodic or continuous administration over an extended period of time, as required. Preferably, administration of the FVIII variant is by intravenous route.

"Factor VIII deficiency," as used herein, includes deficiency in clotting activity caused by production of defective factor VIII, by inadequate or no production of factor VIII, or by partial or total inhibition of factor VIII by inhibitors. Hemophilia A is a type of factor VIII deficiency resulting from a defect in an X-linked gene and the absence or deficiency of the factor VIII variant it encodes.

The FVIII variants of the invention are used to treat uncontrolled bleeding due to factor VIII deficiency (e.g., intraarticular, intracranial, or gastrointestinal hemorrhage) in hemophiliacs.

In an embodiment of the invention, the factor VIII deficiency is hemophilia A.

In another embodiment, the factor VIII deficiency is acquired hemophilia.

In an embodiment, the factor VIII deficiency is treated in patients having developed human FVIII antibodies.

As mentioned above, the FVIII variants of the invention have increased specific activity. It is therefore possible to administer reduced amounts of FVIII variant in order to treat VIII deficiency in accordance with the present invention. The amounts of FVIII variant can be reduced by at least 30%, 35%, 40%, 45%, 50%, 55%, 60% as compared to therapy with a FVIII product that does not contain the up to 27 amino acid deletion of the invention.

Reducing the amount of FVIII variant therapy has the advantage of expected reduced immunogenicity, i.e. it is expected that the probability of generation of inhibitory antibodies against the FVIII replacement therapy in the patient is significantly reduced.

In an embodiment, a factor VIII variant of the invention is administered in an amount of no more than 200 μg/dose or 150 μg/dose or 145 μg/dose or 140 μg/dose or 136 μg/dose or 130 μg/dose.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning a range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EXAMPLES

Example 1

Expression of Recombinant Porcine Partially B-Domain Deleted FVIII (OBI-1) And Isolation of Three Variant Proteins (rpVIIIv1, v2 and v3)

Expression of OBI-1 in BHK cells was carried out essentially as described in U.S. Pat. No. 6,458,563. Three variants were detected in the produced material (rpVIIIv1, v2 and v3). The variants were isolated and purified to >95% purity ion exchange chromatography. For purification, an AKTA Explorer system (AKTA Explorer 10, GE Healthcare Lifesciences #17-5167-01) using a MonoQ HR10/10 semi-preparative anion exchange column (now Mono Q 10/100 GL, GE Healthcare Lifesciences #17-5167-01) was used. Elution was carried out on a gradient with the two following buffers:

Buffer A: 10 mM TRIS, pH 7.0, 0.01% Polysorbate 80

Buffer B: Buffer A and 1 M sodium chloride.

The purification method characteristics are summarized in Table 1.

TABLE 1 rpFVIII Variant Purification Method

| | | |
|---|---|---|
| AKTA Method: | LoopMQ1010 | |
| Flow: | 4 ml/min | |
| Equilibrium Column | 8 CV | |
| Load flow | 4 ml/min | |
| Sample Volume | 40-1000 ml | |
| Wash Column | 10 CV | |
| Gradient | Column Volume (CV) | % B |
| | 7 | 45 |
| | 4 | 50 |
| | 4 | 50 |
| | 6 | 52 |
| | 4 | 52 |
| | 2 | 55 |
| | 7 | 60 |
| | 1 | 65 |
| | 5 | 65 |
| | 1 | 70 |
| | 5 | 70 |
| | 1 | 100 |
| | 7 | 100 |
| | 1 | 10 |
| | 4 | 10 |
| Total Run | 59 CV | |
| Column Temp | Not controlled | |

Example 2

Variant 3 (rpVIIIv3) has a Significantly Higher Specific Activity than Variants 1 and 2

The specific activity of each variant was assessed by dividing the potency assessed by one stage coagulation assay (OSCA) by the protein concentration as measured by the SEC HPLC per method. The OSCA and SEC HPLC methods were carried out as described in "Materials and Methods" Example 5.

Results

The results for the specific activities are indicated in Table 2.

TABLE 2

Specific Activities (OSCA method) for Purified Variants 1, 2 and 3 obtained from two different lots of rpFVIII

| Sample based on SEC | OSCA units/ml | % RSD* | Specific activity units/ml | % RSD* |
|---|---|---|---|---|
| V1 - lot 1 | 1060 | 1.5 | 11956 | 1.7 |
| V2 - lot 1 | 715 | 2.7 | 17267 | 3.3 |
| V3 - lot 1 | 216 | 1.2 | 25926 | 2.8 |
| OBI-1 | 513 | 1 | 18150 | 1.3 |
| V1 - lot 2 | 980 | 1.2 | 12532 | 1.5 |
| V2 - lot 2 | 613 | 0.6 | 16089 | 1.3 |
| V3 - lot 2 | 280 | 2.9 | 19718 | 4.1 |
| OBI-1 | 565 | 4.0 | 14427 | 4.4 |

*relative standard deviation

The observation of significantly higher specific activity for variant 3 in the OSCA assay is distinct and consistent. Since the OSCA method is predictive and representative for the coagulation process in humans, it is expected that variant 3 is a product of significant value. It is expected that 1.5-2.0 fold increase in potency reduce the amount of FVIII administered to patients and might therefore indirectly reduce the occurrence of immunological side effects.

Example 3

Sequence Determination of rpFVIIIv3

The sequence of purified v3 was determined by peptide map followed by LCMS (liquid chromatography mass spectrometry) and LCMS/MS (liquid chromatography mass spectrometry/mass spectrometry) on a Q-TOF Ultima Mass Spectrometer, running MassLynx 4.0 (Waters Corporation, Milford, Mass.).

Approximately 250 µg of Variant 3 was concentrated using an Amicon, Centricon YM-10 concentrator with a 10,000 MWCO filter (Millipore Corporation, Billerica, Mass.) to a volume of <100 µL. The samples were mixed with 450 µL of 6 M guanidine HCl/0.002 M EDTA (ethylenediaminetetraacetic acid)/0.02 M Tris buffer pH 8 and transferred to 2.0 mL polypropylene tubes. 1 M DTT (dithiothreitol) was added to each sample to a final concentration of 10 mM and incubated for 1 hour at 37° C. After reduction, 2 M iodoacetamide was added to each tube to a final concentration of 20 mM and incubated for an additional hour at room temperature. The reduced and alkylated samples were transferred to dialysis cassettes and dialyzed for 1 hour against 1 L of 50 mM ammonium bicarbonate dialysis buffer containing 1.0 M urea, pH 8. The samples were then dialyzed against 1 L of dialysis buffer overnight at room temperature while maintaining constant stirring. After dialysis the final volumes were approximately 0.5 mL each. Samples were divided into two 125 µg aliquots.

After dialysis, the protein sample was contained in a matrix that is optimal for proteolytic digestion with trypsin. Trypsin was added to each sample at an enzyme to substrate ratio of 1:20 (w:w) and incubated for 8 hours at 37° C. All samples were transferred to HPLC vials and analyzed by HPLC-MS.

Reduced and alkylated protein was injected onto a Vydac C18 reverse phase column (Grace, Deerfield, Ill.). Prior to the sample injection, a blank sample (Mobile Phase A; deionized water containing 0.2% (v:v) formic acid) was analyzed to equilibrate the column and demonstrate the absence of interfering peaks.

Mass spectrometry data was collected on a Q-TOF API-US mass spectrometer or a Q-TOF Ultima mass spectrometer (Waters Corporation, Milford, Mass.) using electrospray ionization (ESI) in the positive ion mode. Prior to sample analysis, the mass spectrometer was calibrated using a 5th order fit on the fragment ions of Glu-Fibrinogen peptide covering a range of 175 to 1285 m/z. For the calibration to pass specifications, a RMS (root mean square) error for the mass of the peptide fragments less than 5 ppm was required. The software package Masslynx 4.0™ SP2 and SP4 (Waters Corporation, Milford, Mass.) were used for data acquisition and analysis.

Both MS and MS/MS data were collected using a single liquid chromatography (LC) run. Full mass spectrometer (MS) survey scans were collected from 200-1950 m/z.

The sequence of rpFVIII was determined to correspond to SEQ ID NO: 1. This sequence contains a 27 amino acid deletion in comparison with the OBI-1 sequence.

Example 4 rpFVIIIv3 has a Higher Specific Activity than Other Known FVIII Products

The specific activity of rpFVIIIv3 was compared to three commercially available FVIII products, namely Xynthia® (a recombinant, B-domain deleted human FVIII from Wyeth Pharmaceuticals (Philadelphia, Pa.)), Kogenate FS® (a full-length human FVIII from Bayer Healthcare (Tarrytown, N.Y.)) and Advate® (a full-length human FVIII from Baxter (Westlake Village, Calif.)), as well as to OBI-1 (a recombinant partially B-domain deleted porcine FVIII), which is presently under clinical development, and a B-domain deleted canine factor VIII (Denise E. Sabatino et. al., Recombinant canine B-domain—deleted FVIII exhibits high specific activity and is safe in the canine hemophilia A model, Blood, 12 Nov. 2009, Vol. 114, No. 20, pp. 4562-4565).

The specific activity of OBI-1 and rpFVIIIv3 was determined by the methods as described in Example 5.

The results are depicted in Table 3 and FIG. 1. Due to its increased specific activities, lower amounts of prVIIIv3 per dose can be administered to a patient. It is expected that this decrease in dose will lead to a reduced immunogenicity, i.e. result in a lower probability that patients develop inhibitory antibodies.

TABLE 3

Specific activities of FVIII products as compared to rpVIIIv3

| | Specific Activity in IU/mg Protein | Amt protein µg/dose^ |
|---|---|---|
| Xynthia | 7500 | 400 |
| Kogenate FS | 4000 | 750 |
| Advate | 4000 | 750 |
| OBI-1 | 11000 | 273 |
| rpVIIIv3 | 22000 | 136 |
| Canine BDD* FVIII | 34000 | 88 |

^Amt Protein = xxxx µg/dose. The numbers shown in the column for rpVIII3 mean that an amount of 136 µg per dose will be required. One dose is the required amount to raise the blood factor VIII level from 0% to 100%, i.e. the higher the specific activity (XXX units/mg), the less amount (in terms of µg) is required. Note that 1 mg = 1000 µg. Given that a typical dose is 3000 units per patient, the amount of actual protein required = 3000/22000 = 0.136 mg = 136 µg.
*BDD stands for B-domain deleted and FL stands for full length In conclusion, these results show that rpVIIIv3 has a significantly higher specific activity than the tested products that are presently commercialized, or under clinical development, for FVIII replacement therapy.

In particular, it is highly surprising a deletion of 27 amino acids, present in rpVIIIv3 but not in OBI-1, leads to a 50% increase in specific activity (as measured by the OSCA assay).

Example 5

Materials and Methods

One-Stage Coagulation Assay—Osca—Method
1. Dilute Reference Standard in Assay Buffer (10% Factor VIII deficient plasma+Owren's Veronal Buffer, per liter, 28 mmol of sodium barbital and 125 mmol of NaCl, pH 7.35) to target potency of 1.0 units/mL.
2. Dilute check standards, activity controls and samples in Assay Buffer to the target potency.
3. Load the calibration standard (reference) and reagents into the appropriate wells inside a Symex instrument. (Sysmex CA-1500, Coagulation Analyzer, Dade Behring #B4260-1500 (Siemans Corporation, Deerfield, Ill.)).
4. Load check standard, controls and samples into racks outside of the Sysmex instrument.
5. Assay sequence occurs automatically inside the instrument as follows:
   a. 5 uL of sample is diluted into 45 ul of assay buffer inside the reaction tube
   b. 50 ul of factor VIII deficient plasma is added to the reaction tube
   c. 50 ul of Dade Actin FS (purified soy phosphatides in $1.0 \times 10^{-4}$ M Ellagic acid activator, Dade Behring, Liederbach, Germany) activated partial thromboplastin time reagent is added to the reaction tube and incubated for 60 seconds.
   d. 50 ul of Calcium Chloride (0.025M, Dade Behring, Liederbach, Germany) is added to the reaction tube and incubated for 240 seconds.
   e. The clot time is measured up to a maximum time of 300 seconds.
6. The clot time is then correlated to the potency generated by the reference standard calibration curve.

Size-Exclusion (Sec) HPLC Method

An Agilent 1100 (Agilent Technologies, Santa Clara, Calif.) or a Waters Bioalliance HPLC system (Waters Corporation, Milford, Mass.) was and is typically used for the size exclusion method for determination of protein concentration. The typical size exclusion column used was a Superdex 200 from GE (Superdex 200 10.300 GL, 10×300 mm, Cat #17-5175-01 (GE Healthcare Lifesciences, Piscataway, N.J.)). A general assay protocol is as follows:
1. A typical mobile phase was prepared that contained 400 mM NaCl with 20 mM TRIS, pH 7.4 and 0.01% polysorbate 80.
2. The mobile phase was run through the HPLC system and column until equilibration of the baseline was observed.
3. Standards were run to establish system suitability with a typical run time of 30 minutes for each sample.
4. Samples were typically loaded onto an auto sampler with a control chamber temperature of 4° C.
5. A calibration standard of known concentrations containing various amounts of standard samples, typically from 1, 3, 5, 10 and 25 µg of protein were loaded onto the column in volumes between 10 to 50 µl.
6. Samples of unknown concentrations were also loaded into the columns typically in volumes between 30 to 50 µl.
7. The HPLC system was programmed to run the samples automatically according the sequence set up.
8. The peak area of the calibration standards and the unknown samples were determined based on fluorescence detection with excitation and emission at 280 nm and 340 nm respectively.
9. A linear regression of the calibration standards was generated and the concentration of the unknown sample was determined against this calibration curve.

Figure 3:
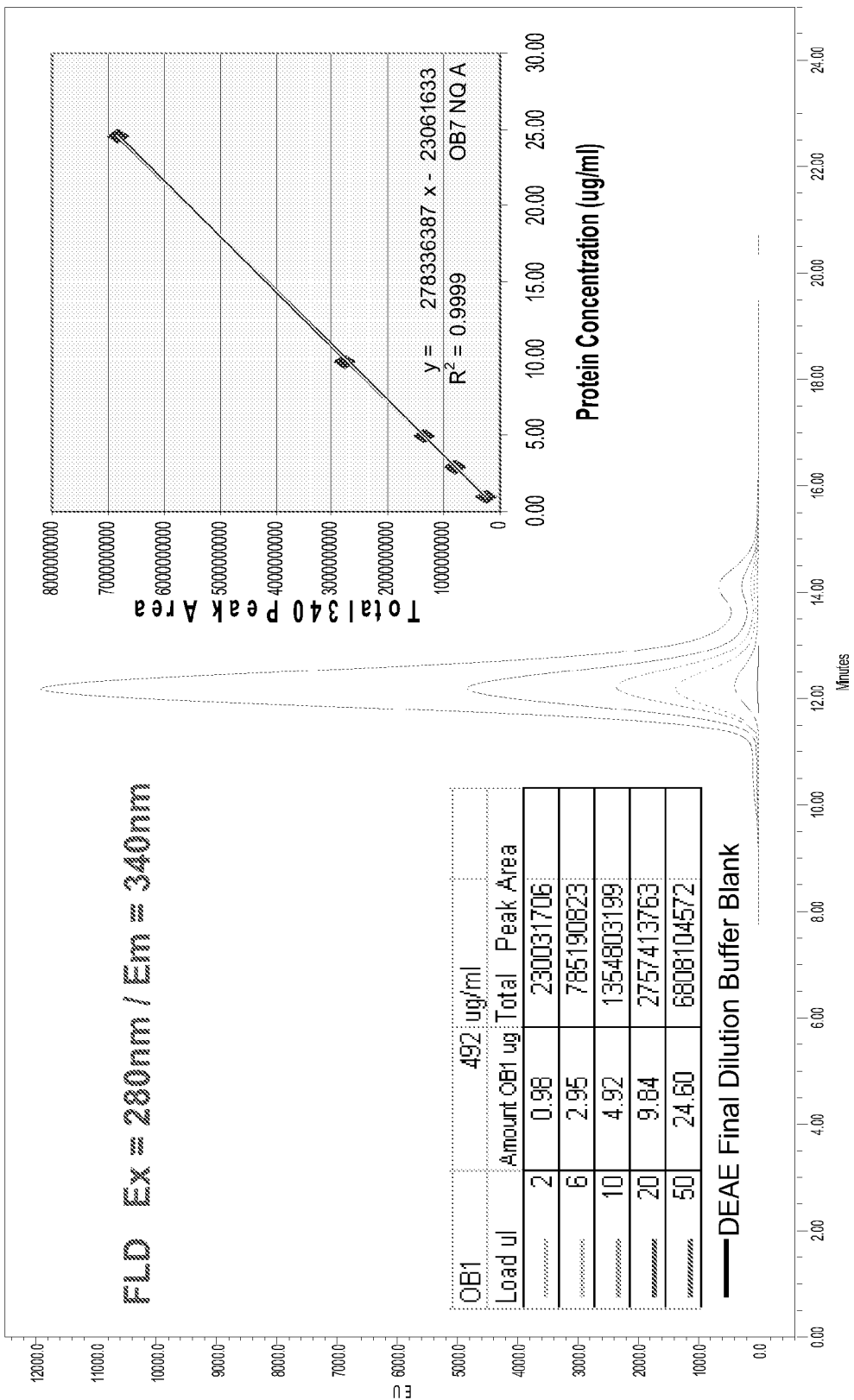
FIG. 3 shows typical example of the SEC profile of the calibration standards and the linear regression of the calibration curve as described in Example 5.

A typical example of the SEC profile of the calibration standards and the linear regression of the calibration curve is shown in FIG. 3.

Example 6

Binding to von Willebrand Factor

Von Willebrand factor (vWF) is a multifunctional glycoprotein which circulates in plasma as a multimeric form complexed with Factor VIII (FVIII/vWF complex). The FVIII/vWF complex serves to protect the bound FVIII from early proteolysis in circulation in vivo.

Size exclusion chromatography (SEC) is used to characterize the binding in FIII/vWF complexes. A Superose 6 column (Superose 6 10/300GL, GE Healthcare #17-5172-01, flow rate=0.5 mL/min) was selected for its known biocompatibility and high exclusion limit of 40 million Daltons (Mobile Phase formulation buffer: 2 mM CaCl2, 10 mM Tris pH 7.0, 300 mM NaCl, 0.01% PSB-80, 11 mM sucrose, 10 mM trisodium citrate). The differences in molecular weight between von Willebrand factor (dimeric @~500 KD, Fitzgerald Cat#30C-CP4003U, Lot #A09121050, Monomer Mol. Wt=~260 kD, Conc.=77 µg/mL) and rpFVII (~160 KD) is sufficient to resolve the two species.

The stoichiometry of binding was determined by titration of constant amount of vWF with increasing amounts of rpFVIII. The profile of the complexation formation between rpFVIII and vWF was determined from the SEC chromatogram and integration of the appropriate peaks. The soluble form of the resultant mixtures in the supernatant were used to determine the end point of the complexation from titration with increasing amounts of rpFVIII. The larger, stable complexes formed between rpFVIII and vWF migrate from the normal retention time to the exclusion limit of the column. When saturation occurs, increasing amounts of unbound rpFVIII will be observed in the SEC chromatogram. This method is used to distinguish differences and similarities in the properties of the variants.

Example 7

Thrombin Digestion Kinetics

SDS-PAGE

Recombinant porcine factor VIII (rpFVlll) molecules are heterodimers of approximately 160 kD composed of a 78.5 kD molecular weight light chain (A3-C1-C2, 765-1448) and a heavy chain ranging in molecular weight from 86.7 kD (A1-A2). The heavy chain of rpFVIII is heterogeneous and composed of three main variants which are formed upon secretion from the cell and may be cleaved by membrane bound proteases of the subtilisin family designated PACE (Paired Basic Amino Acid Cleavage Enzyme).

Like the human factor VIII, rpFVIII is transformed into an active form by limited proteolysis from thrombin. Thrombin activation of rpFVIII is specific for the cleavage site of the heavy chain at Arg(372)-Ser(373). The cleavage region for the Light Chain at Arg(805)-Ser(806) liberates a small 40 amino acid peptide fraction ranging from 765-804 (~4.4 kD). The combination of these initial cleavages by thrombin form the activated recombinant porcine factor VIII as a heterotrimer of subunits designated as A1 (~50 kD), A2 (~40 kD), and A3-C1-C2 (~70 kD). The cleaved rpFVIII A1 and A3-C1-C2 subunits retain the divalent metal ion-dependent linkage, whereas the A2 subunit is weakly associated with the A1-A3-C1-C2 dimer by primarily electrostatic interactions. In SDS-PAGE, these subunits are displayed as three distinct bands. The efficiency in conversion of the rpFVIII (2 peptide units) to three peptide units is characteristic of thrombin activation of the product. This method distinguishes the similarity and differences between the individual variants.

Two other orthogonal methods can be and were used to map the kinetics of thrombin digestion of FVIII. Denaturing reverse phase HPLC may be used; the peak profiles are expected to be similar to that of SDS-PAGE. Anion exchange chromatography, which retains the native form of the peptides, may also be used.

Reverse Phase HPLC

Equipment:
1. HPLC 1100 series: Agilent Technologies, Santa Clara, Calif., USA; Model No. 61312A, Serial No. DE10907753.
2. Poroshell 5 um 2.1×75 mm column: Agilent Technologies, Santa Clara, Calif., USA; Part No. 660750-909, Serial No. USVV001988.

Reagents:
1. Buffer A: 0.1% TFA (JT B Baker, Phillisburg, N.J.; Cat No. 94700-00, Lot No. J23J00) in water
2. Buffer B: 0.1% TFA in Acetonitrile (JT Baker, Phillisburg, N.J.; Cat No. 9017-03, Lot No. J38807).

Procedure:
1. Equilibrate the column for 60 minutes using 99% A and 1% B at 1 ml/min.
2. Sample injections were 50 µl in volume; 25 µl of reference standard was used as control.
3. An example of the method used to run the samples is shown Table 4.

TABLE 4

| Injection | Time (min) | Flow (ml/min) | % A | % B |
|---|---|---|---|---|
| 1 | 0.00 | 2 | 99 | 1 |
| 2 | 2.00 | 2 | 99 | 1 |
| 3 | 3.00 | 2 | 64 | 36 |
| 4 | 3.50 | 2 | 64 | 36 |
| 5 | 4.00 | 2 | 61 | 39 |
| 6 | 5.00 | 2 | 61 | 39 |
| 7 | 5.10 | 2 | 58 | 42 |
| 8 | 6.50 | 2 | 58 | 42 |
| 9 | 6.51 | 2 | 56 | 44 |
| 10 | 7.20 | 2 | 56 | 44 |
| 11 | 7.21 | 2 | 40 | 60 |
| 12 | 8.50 | 2 | 40 | 60 |
| 13 | 8.51 | 2 | 10 | 90 |
| 14 | 9.00 | 2 | 10 | 90 |
| 15 | 9.10 | 2 | 99 | 1 |
| 16 | 10.00 | 2 | 99 | 1 |

Anion Exchange Chromatography

Equipment:
1. AllianceBio HPLC, Waters corporation, Milford, Mass., USA; Model No. 2796; Serial No M08BA1199M.
2. Protein Pak Hi Res Q 5 um 4.6×100 mm column: Waters Corporation, Milford, Mass., USA; Part No. 186004931, Serial No. 502N112561VE04.

Reagents:

Buffer A:
10 mM Tris base (1.211 g/L)
2 mM Calcium Chloride (0.588 g/L)
0.01% polysorbate 80 (1 ml of 10% PS-80/L)
Filtered water up to 1 L, pH 7.0

Buffer B:
10 mM Tris base (1.211 g/L)
2 mM Calcium Chloride (0.588 g/L)
0.01% polysorbate 80 (1 ml of 10% PS-80/L)
1M Sodium Chloride (58.44 g/L)
Filtered water upto 1 L, pH 7.0

Procedure:
1. Equilibrate the column for 60 min using 70% A and 30% B at 0.5 ml/min
2. Sample injections were 50 µl in volume; 10 µl of reference standard was used as control.
3. An example of the method used to run the samples is shown Table 5.

TABLE 5

| Injection | Time (min) | Flow (ml/min) | % A | % B |
|---|---|---|---|---|
| 1 | 0.01 | 0.5 | 70 | 30 |
| 2 | 0.50 | 0.5 | 70 | 30 |
| 3 | 3.50 | 0.5 | 60 | 40 |
| 4 | 5.00 | 0.5 | 60 | 40 |
| 5 | 10.00 | 0.5 | 30 | 70 |
| 6 | 10.10 | 0.5 | 1 | 99 |
| 7 | 12.00 | 0.5 | 1 | 99 |
| 8 | 12.10 | 0.5 | 70 | 30 |
| 9 | 17.00 | 0.5 | 70 | 30 |

The skilled artisan would know and appreciate that these and other methods may be used to arrive at understanding recombinant Factor VIII proteins as described herein.

The invention claimed is:

1. An isolated and recombinant, fully or partially B-domain deleted porcine factor VIII (FVIII) variant, the FVIII variant being devoid of an amino acid sequence corresponding to amino acids 716 to 742 of porcine factor VIII as depicted in FIG. 2 or amino acids 714 to 740 of SEQ ID NO: 7.

2. The FVIII variant according to claim 1, comprising a sequence being at least 90% identical to SEQ ID NO: 1, the variant being devoid of the amino acid sequence corresponding to amino acids 716 to 742 of porcine factor VIII as depicted in FIG. 2 or amino acids 714 to 740 of SEQ ID NO: 7.

3. The FVIII variant according to claim 2, wherein said variant shares at least 95% identity to SEQ ID NO:1.

4. The FVIII variant according to claim 3, wherein said variant shares at least 99.5% identity to SEQ ID NO: 1.

5. The FVIII variant according to claim 4, wherein said variant is SEQ ID NO:1.

6. The FVIII variant according to claim 1, wherein the FVIII variant is partially B-domain deleted and the remaining portion of the B-domain is SEQ ID NO: 4.

7. A pharmaceutical composition comprising a factor VIII variant according to claim 1.

8. A method of treating a patient suffering from hemophilia comprising administering a therapeutically effective amount of FVIII variant according to claim 1 to a patient in need thereof, thereby treating the hemophilia in said patient.

9. The method according to claim 8, wherein said hemophilia is hemophilia A.

10. The method according to claim 8, wherein said hemophilia is acquired hemophilia.

11. The method according to claim 8, wherein said patient has human FVIII antibodies.

12. The method according to claim 8, wherein the factor VIII variant is administered in an amount of no more than 200 µg/dose.

* * * * *